US008143478B2

(12) United States Patent
Umemoto et al.

(10) Patent No.: US 8,143,478 B2
(45) Date of Patent: Mar. 27, 2012

(54) PEPTIDE TRANSPORTING TO CHROMOPLASTS IN PETALS AND METHOD OF CONSTRUCTING PLANT HAVING YELLOWISH PETALS BY USING THE SAME

(75) Inventors: Naoyuki Umemoto, Tichigi (JP); Toshihiro Toguri, Tochigi (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 1167 days.

(21) Appl. No.: 11/791,513

(22) PCT Filed: Nov. 29, 2005

(86) PCT No.: PCT/JP2005/022261
§ 371 (c)(1),
(2), (4) Date: May 24, 2007

(87) PCT Pub. No.: WO2006/057462
PCT Pub. Date: Jun. 1, 2006

(65) Prior Publication Data
US 2008/0016597 A1 Jan. 17, 2008

(30) Foreign Application Priority Data
Nov. 29, 2004 (JP) ................. 2004-344059

(51) Int. Cl.
*C12N 15/29* (2006.01)
*C12N 15/52* (2006.01)
*C12N 15/82* (2006.01)
(52) U.S. Cl. ...... 800/282; 800/298; 536/23.2; 536/23.6; 435/320.1; 435/419
(58) Field of Classification Search .................. 800/282, 800/298; 536/23.2, 23.6
See application file for complete search history.

(56) References Cited

U.S. PATENT DOCUMENTS
2004/0237147 A1* 11/2004 Habben et al. ................ 800/294

FOREIGN PATENT DOCUMENTS
| JP | 9-510608 | | 10/1997 |
| JP | 2002-516567 | | 6/2002 |
| WO | WO 03/080849 | * | 2/2003 |
| WO | WO 03/080849 A2 | | 10/2003 |
| WO | WO 2004/074442 A2 | | 9/2004 |
| WO | WO 2005/019460 A2 | | 3/2005 |

OTHER PUBLICATIONS

Vishnevetsky M. et al.,The Plant Journal vol. 10, No. 6; pp. 1111-1118.*

Sakakibara, H et al. PNAS Jul. 12, 2005; vol. 102, No. 28; pp. 9972-9977.*
Kumagai, M. et al., The Plant Journal; (1998) vol. 14, No. 3; pp. 305-315.*
European Search Report EP 09 17 0168 dated Oct. 26, 2009.
Database UniPort [Online], Apr. 1, 1990, "RecName: Full=Isopentenyl transferase: AltName: Full=Dimethylallyl transferase; EC=<AHREF=http://srs.ebi.ac.uk/srsbin/cei-bin/wgetz?[enzyme- ECNumber:2.5.1.*]+–e >2.5.1.-</A>;" XP002552325 Retrieved from EBI accession No. UNIPROT:P15653 Database accession No. P15653.
European Search Report Application No. 05811312.7—Dec. 10, 2008.
Varda Mann et al., "Metabolic engineering of astaxanthin production in tobacco flowers", Nature Biotechnology, vol. 18, No. 8, Aug. 1, 2000, pp. 888-892.
Naoyuki Umemoto et al., "Flower color modification by xanthophyll biosynthetic genes in petunia", Plant and Cell Physiology, vol. 47, No. Suppl. S, 2006, pp. 5110, XP009108928 & 47$^{TH}$ Annual Meeting of the Japanese-Society-Of-Plant-Physiologists, Tsukuba, Japan, March 19-21, 2006.
Michael Vishnevetsky et al., "Molecular cloning of a carotenoid-associated protein from *Cucumis sativus* corollas: homologous genes involved in carotenoid sequestration in chromophasts", The Plant Journal (1996) 10 (6), pp. 1111-1118.
Elena Monte et al., "Leaf C40.4: a carotenoid-associated protein involved in the modulation of photosynthetic efficiency?", The Plant Journal (1999) 19(4), pp. 399-410.
Benjamin Gillet et al., "Molecular characterization of CDSP 34, a chloroplastic protein induced by water deficit in *Solanum tuberosum* L. plants, and regulation of CDSP 34 expression by ABA and high illumination", The Plant Journal (1998) 16(2), pp. 257-262.
J. Deruere et al., "Structure and Expression of Two Plant Genes Encoding Chromoplast-Specific Proteins: Occurrence of Partially Spliced Transcripts", Biochemical and Biophysical Research Communications, vol. 199, No. 3, 1994, Mar. 30, 1994, pp. 1144-1150.
Geraldine Bonnard et al., "Nucleotide sequence, evolutionary origin and biological role of a rearranged cytokin gene isolated from a wide host range biotype III Agrobacterium strain", Mol Gen Genet (1989), 216: 428-438.
Timothy J. Strabala et al., "Isolation and characterization of an *ipt* gene from the Ti plasmid Bo542", Mol. Gen. Genet. (1989) 216: 388-394.

* cited by examiner

*Primary Examiner* — Russell Kallis
(74) *Attorney, Agent, or Firm* — Stephen A. Bent; Foley & Lardner LLP

(57) ABSTRACT

It is an object of the present invention to provide a means of imparting a yellowish flower color to a plant having no or little yellowish flower color or enhancing the yellowish flower color in a plant.
In accordance with the present invention, a method of producing a plant having yellowish petals with the use of a peptide having transport activity to chromoplasts in petals and a fused gene formed of a gene encoding such peptide and one, or two or more genes encoding enzyme proteins involved in the carotenoid biosynthetic pathway is provided.

7 Claims, 7 Drawing Sheets
(3 of 7 Drawing Sheet(s) Filed in Color)

FIG. 1

[Genetyx-win: amino acid sequence homology data]

1st Amino acid sequence (SEQ ID NO: 2)

File name: Petunia

Sequence size: 59

2nd Amino acid sequence (SEQ ID NO: 35)

File name: Pisum sativum

Sequence size: 61

Unit size compared = 2

Pickup position = 1

[26.667% / 15 aa]    INT/OPT.Score : < 15/ 30>

1st amino acid sequence (petunia) (SEQ ID NO: 2):

MASI SSLNQFPCKT LQLTSQFSKP TSNISSFPIF SSKTEQQKPI SLQEYTNTRS RVTVK

2nd amino acid sequence (Pisum sativum) (SEQ ID NO: 35):

MASMISSSAV TTVSRASRGQ SAAVAPFGGL KSMTGFPVKK VNTDITSITS NGGRVKCMVL D

Fig. 4
Nontransformant
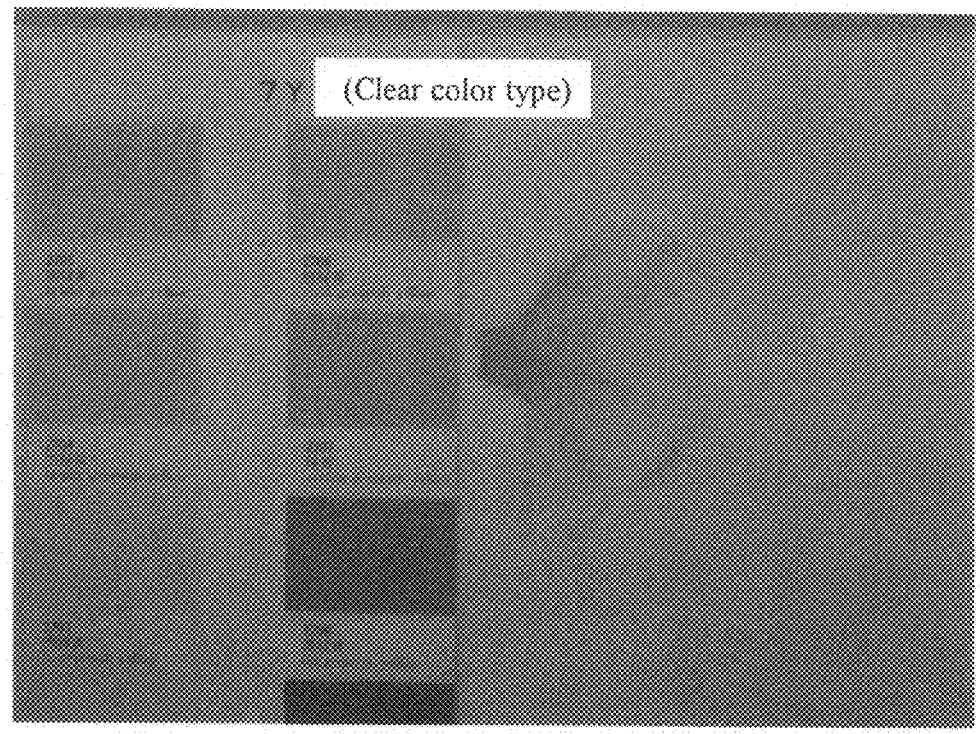
pKT123 no.33
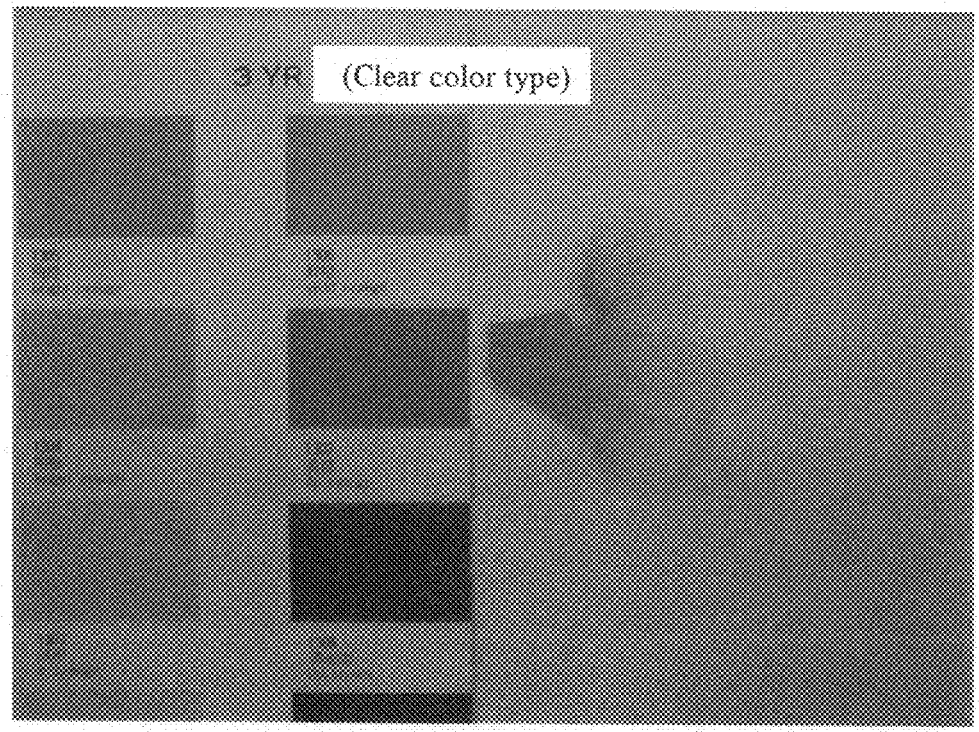

Left: Nontransformant
Right: pKT139

PEPTIDE TRANSPORTING TO CHROMOPLASTS IN PETALS AND METHOD OF CONSTRUCTING PLANT HAVING YELLOWISH PETALS BY USING THE SAME

CROSS REFERENCE TO RELATED PATENT APPLICATIONS

The present application is the US National Stage of PCT/JP2005/022261, filed Nov. 29, 2005, which claims benefit of Japanese Patent Application No. 2004-344059, filed Nov. 29, 2004, which are incorporated herein by reference in their entirety.

TECHNICAL FIELD

The present invention relates to a peptide (transit peptide) having transport activity to petal chromoplasts and also relates to a method of constructing a plant having yellowish petals (a color tone ranging from yellow through orange to red) using the same. Specifically, the present invention relates to a method of producing a plant having yellowish petals by introducing genes encoding different enzyme proteins involved in the carotenoid biosynthetic pathway, to which sequences of transit peptides that transport to petal chromoplasts have been ligated, into a plant having petals having no or little yellowish color due to dysfunction of enzymes involved in the carotenoid biosynthetic pathway or due to low levels of activity of such enzymes.

BACKGROUND ART

The most important property of ornamental flowers is flower color. In particular, a yellowish flower color (a color tone ranging from yellow through orange to red) is important. Hitherto, in order to obtain a clear yellowish flower color, breeding has been carried out via crossing. In the cases of roses, older types of garden roses that have been used as ornamental flowers have no yellowish flower color. Thus, a deep yellowish flower color has been imparted to roses via introduction of *Rosa foetida* that has been found in the West Asia [Hideaki Ooba, Chuko Shinsho, The Birth of Roses (*Bara no Tanjo*) (1990)]. Also in the case of iris (*Iris ensata* var. *ensata*), a yellowish flower color has been imparted thereto via crossing of allied species of *Iris pseudacorus* [Tsutomu Yabuya, Seibundo Shinkosha Inc., *Biohorti*, 1, 64-71 (1990)]. However, in the cases of breeding via crossing as described above, the existence of a wild species having yellow color, which can be hybridized, is necessary. In addition, such crossing is very time- and labor-consuming. Actually, in the cases of petunias, asters, gentians, salvias, and the like, which are important horticulture plants, no plants having a clear yellowish color have been obtained through conventional breeding via crossing.

The yellowish flower color is mainly derived from carotenoid or betalain in many cases. In some cases, such color is derived from a flavonoid. In particular, a clear yellowish flower color is often derived from carotenoid.

In the cases of carotenoids (e.g. carotenoids in a broad sense, including xanthophylls having a substituent comprising oxygen [Norio Saito, Seibundo Shinkosha Inc., *Biohorti*, 1, 49-57 (1990)]), as a gene involved upstream of the carotenoid biosynthetic pathway from farnesyl diphosphate (FPP) through geranylgeranyl pyrophosphate (GGPP) to β-carotene, genes encoding enzyme proteins such as a GGPP synthase derived from *Ervinia uredovora*, a phytoene synthase, a lycopene synthase, and a β-cyclase have been isolated by Misawa et al. (JP Patent No. 2950888). Thereafter, isolation of carotenoid-metabolic genes from various types of microorganisms or plants has progressed (WO2003/016503). In addition, genes (ketolase genes) involved in the synthesis of ketocarotenoids (e.g., canthaxanthin and astaxanthin) have been obtained by Misawa et al. from microorganisms (JP Patent No. 3375639) and green algae (JP Patent No. 2960967). Also, ketolase genes have been obtained from the yeast *Phaffia rhodozyma* (U.S. Pat. No. 6,365,386) and plants derived from the *Adonis aestivalis* (WO99/61625). Further, production of ketocarotenoids (e.g., canthaxanthin and astaxanthin) has been achieved via transformation in microorganisms (*Escherichia coli*) and yeasts [Miura et al., Appl. Env. Microbiol., 64, 1226-1229 (1998)] with the use of such genes. Also in the cases of plants, it has been attempted to produce carotenoids or increase the amount of carotenoids produced with the use of such genes. There have been reports that carotenoids are stored in rice seeds (rice grains) [Ye et al., Science, 287, 303-305 (2000)], rapeseed seeds [Shewmaker et al, Plant J., 20, 401-412 (1999)], and seeds of *Arabidopsis thaliana* [Stalberg et al, Plant J., 36, 771-779 (2003)]. However, in these successful examples, carotenoids are stored in seeds. There have been no reports that the amount of carotenoids produced in petals has been successfully increased. Hirshberg et al. expressed a ketolase gene obtained from green algae in tobacco. However, they reported a failure to cause the expression in petals and the expression was found exclusively in a nectary [Mann et al, Nat. Biotechnol., 18, 888-892 (2000)]. Further, cloning of a gene encoding an enzyme protein of a capsanthin-capsorubin synthase causing generation of yellowish pigment of capsicum has been carried out, such synthase being recognized as a key enzyme synthesizing capsanthin or capsorubin known as a ketocarotenoid [Bouvier et al, Plant J., 6, 45-54 (1994)]. However, such gene has not been used for modification of flower color [Davies et al., Acta Hort., 624, 435-447 (2003)].

The aforementioned reports regarding accumulation of carotenoids in rice seeds (rice grains) [Ye et al., Science. 287, 303-305 (2000)], rapeseed seeds [Shewmaker et al., Plant J., 20, 401-412 (1999)], and the like provide examples of instances of increases in the amount of carotenoid produced via introduction of genes of the carotenoid biosynthetic pathway. Also, there are similar reports regarding microorganisms and yeasts [Kajiwara et al., Biochem J., 324, 421-6 (1997); Shimada et al., Appl Environ Microbiol., 64, 2676-80 (1998); Matthews et al., Appl Microbiol Biotechnol., 53, 396-400 (2000); and Kim et al., Biotechnol Bioeng., 72, 408-15 (2001)]. Various types of enzyme genes existing upstream of the pathway for synthesizing carotene (e.g., a phytoene synthase gene, a lycopene synthase gene (phytoene desaturase), an isopentenyl diphosphate isomerase gene, a hydroxymethylglutaryl CoA (HMG-CoA) reductase gene, and a 1-deoxy-D-xylose-5-phosphate synthase gene) have been used in such cases. It is believed that the carotenoid production may be enhanced by different genes depending on hosts. Accordingly, it is shown that rate-limiting processes in a metabolic pathway significantly vary depending on host, thus making it difficult to determine genes that should be enhanced for increasing the amount of carotenoid produced without trial. In particular, there have been no reports clearly suggesting the production of carotenoid in petals. Thus, it is necessary to introduce carotenoid synthase genes upstream of the pathway alone or in combinations of two or more so as to examine whether or not such introduction is effective for causing a yellowish color to be expressed in petals.

In the cases of plants, carotenoid biosynthesis takes place in a plastid, in general. Plastids are known to differentiate into chloroplasts in the cases of cells in which photosynthesis is carried out in a proplastid with the use of the green color of leaves or stems, leucoplasts that store starch and protein in the cases of cells of white tissues constituting roots and the like, or chromoplasts that store carotenoid in the cases of cells of flowers or fruits. It is also known that these are different cell organellas according to morphlogical observation using an electron microscope.

When a protein derived from nuclear DNA is expressed in a chloroplast, a transit peptide is necessary. In order to cause a gene derived from an organism such as a microorganism lacking chloroplast or a gene expressed outside of a chloroplast to be expressed in a chloroplast, the cDNA sequence of a transit peptide, which is a sequence having a function of transferring a gene product to a chloroplast, is ligated to the front of a gene sequence to be expressed. Thus, a gene product is transferred to a chloroplast [Keegstra, Cell, 56, 247-253 (1989)]. In general, the most widely used sequence is a transit peptide derived from a small subunit of ribulose bisphosphate oxygenase/carboxylase protein (RubisCO) of *Pisum sativum* (garden pea) [Schreier et al., EMBO J., 4, 25-32 (1985) and Misawa et al., Plant J., 4, 833-840 (1993)].

As described above, a transit peptide used for transferring a gene product to a chloroplast has been known. However, there have been no studies of transit peptides involved in carotenoid biosynthesis or protein transport in chromoplasts (particularly in petals). In addition, it is generally believed that transit peptides have no substrate specificity or organ specificity [Jarvis and Soll, Biochemica Biophysica Acta., 1541, 64-79 (2001)]. Thus, there has been an example in which petunias and marigolds were transformed with the use of ketolase genes of microorganisms and green algae obtained by Misawa et al, and it was attempted to cause the expression of such genes in petals (US Patent Publication (Kokai) No. 2004/0003430). In such case, the transit peptide used was a transit peptide derived from a small subunit of RubisCO protein of *Pisum sativum*, which serves as a signal for the aforementioned transport to a chloroplast. Further, in the above reference, changes in flower color were observed only with the use of a strain obtained by hybridizing transformants into which a phytoene synthase gene and a ketolase gene had been introduced, respectively. Furthermore, based on data from the same reference regarding the transformed plants to which the genes had been separately introduced (tables 12-13), it cannot be said that changes in flower colors in petals of transformed plants were visually observed or that accumulation of pigments developing sufficient colors that are valuable in terms of horticulture took place.

Thus, techniques for causing the expression of genes encoding different enzyme proteins involved in the carotenoid biosynthetic pathway in petals have not been established. Therefore, yellowish flower colors have not been imparted to plants having no or little yellowish flower color. In addition, enhancement of such flower color in plants has not been achieved.

Accordingly, it is an objective of the present invention to provide a means of imparting yellowish flower color to a plant having no or little yellowish flower color or enhancing the yellowish flower color of a plant.

DISCLOSURE OF THE INVENTION

As a result of intensive studies in order to achieve the above objectives, the inventors of the present invention have found a novel transit peptide that functions in chromoplasts in petals. They ligated a gene encoding such transit peptide to genes encoding different enzyme proteins involved in the carotenoid biosynthetic pathway and introduced the resultant into plants. Thus, plants having yellowish petals were obtained. This has led to the completion of the present invention.

That is, the present invention encompasses the following inventions.

(1) A peptide which is the following (a) or (b):
  (a) a peptide consisting of the amino acid sequence set forth in SEQ ID NO: 2, 4, 30, 32, or 34; or
  (b) a peptide consisting of an amino acid sequence derived from the amino acid sequence set forth in SEQ ID NO: 2, 4, 30, 32, or 34 by deletion, substitution, insertion, or addition of one or several amino acids and having transport activity to chromoplasts in petals.

(2) A gene encoding a peptide which is the following (a) or (b):
  (a) a peptide consisting of the amino acid sequence set forth in SEQ ID NO: 2, 4, 30, 32, or 34; or
  (b) a peptide consisting of an amino acid sequence derived from the amino acid sequence set forth in SEQ ID NO: 2, 4, 30, 32, or 34 by deletion, substitution, insertion, or addition of one or several amino acids and having transport activity to chromoplasts in petals.

(3) A gene consisting of DNA which is the following (c), (d), or (e):
  (c) DNA consisting of the nucleotide sequence set forth in SEQ ID NO: 1, 3, 29, 31, or 33;
  (d) DNA that hybridizes under stringent conditions to DNA consisting of a nucleotide sequence complementary to DNA consisting of the nucleotide sequence set forth in SEQ ID NO: 1, 3, 29, 31, or 33 and that encodes a peptide having transport activity to chromoplasts in petals; or
  (e) DNA that consists of a nucleotide sequence at least 80% homologous to the nucleotide sequence set forth in SEQ ID NO: 1, 3, 29, 31, or 33 and that encodes a peptide having transport activity to chromoplasts in petals.

(4) A recombinant vector containing a fused gene formed of the gene according to (2) or (3) and one, or two or more genes encoding an enzyme protein involved in the carotenoid biosynthetic pathway.

(5) The recombinant vector according to (4), wherein the enzyme protein involved in the carotenoid biosynthetic pathway is a 1-deoxy-D-xylose-5-phosphate synthase, an isopentenyl diphosphate isomerase, a geranylgeranyl pyrophosphate synthase, a phytoene synthase, a lycopene synthase, a β-cyclase, ketolase, or a capsanthin-capsorubin synthase.

(6) A plant cell into which the recombinant vector according to (4) or (5) has been introduced.

(7) A plant cell into which any one of the following fused genes has been introduced:
  (f) a fused gene formed of a gene consisting of the nucleotide sequence set forth in SEQ ID NO: 1 and a gene consisting of the nucleotide sequence set forth in SEQ ID NO: 5;
  (g) a fused gene formed of a gene consisting of the nucleotide sequence set forth in SEQ ID NO: 1 and a gene consisting of the nucleotide sequence set forth in SEQ ID NO: 9; and
  (h) a fused gene formed of a gene consisting of the nucleotide sequence set forth in SEQ ID NO: 3 and a gene consisting of the nucleotide sequence set forth in SEQ ID NO: 14.

(8) A method of producing a plant having yellowish petals, comprising introducing a fused gene formed of a gene encoding a peptide having transport activity to chromoplasts in petals and one, or two or more genes encoding an enzyme protein involved in the carotenoid biosynthetic pathway into a plant cell and regenerating a plant from the plant cell.

(9) The method according to (8), wherein the peptide having transport activity to chromoplasts in petals is a transit peptide of the fibrillin gene of petunia, a transit peptide of the capsanthin-capsorubin synthase gene of capsicum, or a transit peptide of the cytokinin synthase gene of *Agrobacterium*.

(10) A method of producing a plant having yellowish petals, comprising introducing a fused gene formed of the gene according to (2) or (3) and one, or two or more genes encoding an enzyme protein involved in the carotenoid biosynthetic pathway into a plant cell and regenerating a plant from the plant cell.

(11) The method according to any one of (8) to (10), wherein the enzyme protein involved in the carotenoid biosynthetic pathway is a 1-deoxy-D-xylose-5-phosphate synthase, an isopentenyl diphosphate isomerase, a geranylgeranyl pyrophosphate synthase, a phytoene synthase, a lycopene synthase, a β-cyclase, a ketolase, or a capsanthin-capsorubin synthase.

In accordance with the present invention, a transit peptide that efficiently transports to petal chromoplasts is provided. With the use of such peptide, it is possible to impart yellowish flower color to plants that have had no or little yellowish flower color (a color tone of which ranges from yellow through orange to red) or enhance a yellowish flower color of such plants by introducing genes encoding different enzyme proteins involved in the carotenoid biosynthetic pathway into such plants.

BRIEF DESCRIPTION OF THE DRAWINGS

The application contains at least one drawing executed in color. Copies of this patent or patent application publication with color drawing(s) will be provided by the Office upon request and payment of the necessary fee.

FIG. 1 shows results of analysis of the amino acid sequence of a transit peptide expected from the cDNA sequence of petunia fibrillin of the present invention the first amino acid sequence, SEQ ID NO: 2) and an amino acid sequence of a known transit peptide of *Pisum sativum* (the second amino acid sequence, SEQ ID NO: 35) with the use of DNA analysis software GENETYX (ver. 4.0, GENETYX CORPORATION), indicating that significant homology therebetween was not observed.

FIG. 4 shows results of comparison of petals of a transformant transformed with pKT123 and those of a nontransformant according to the JHS color chart.

Figure 2:
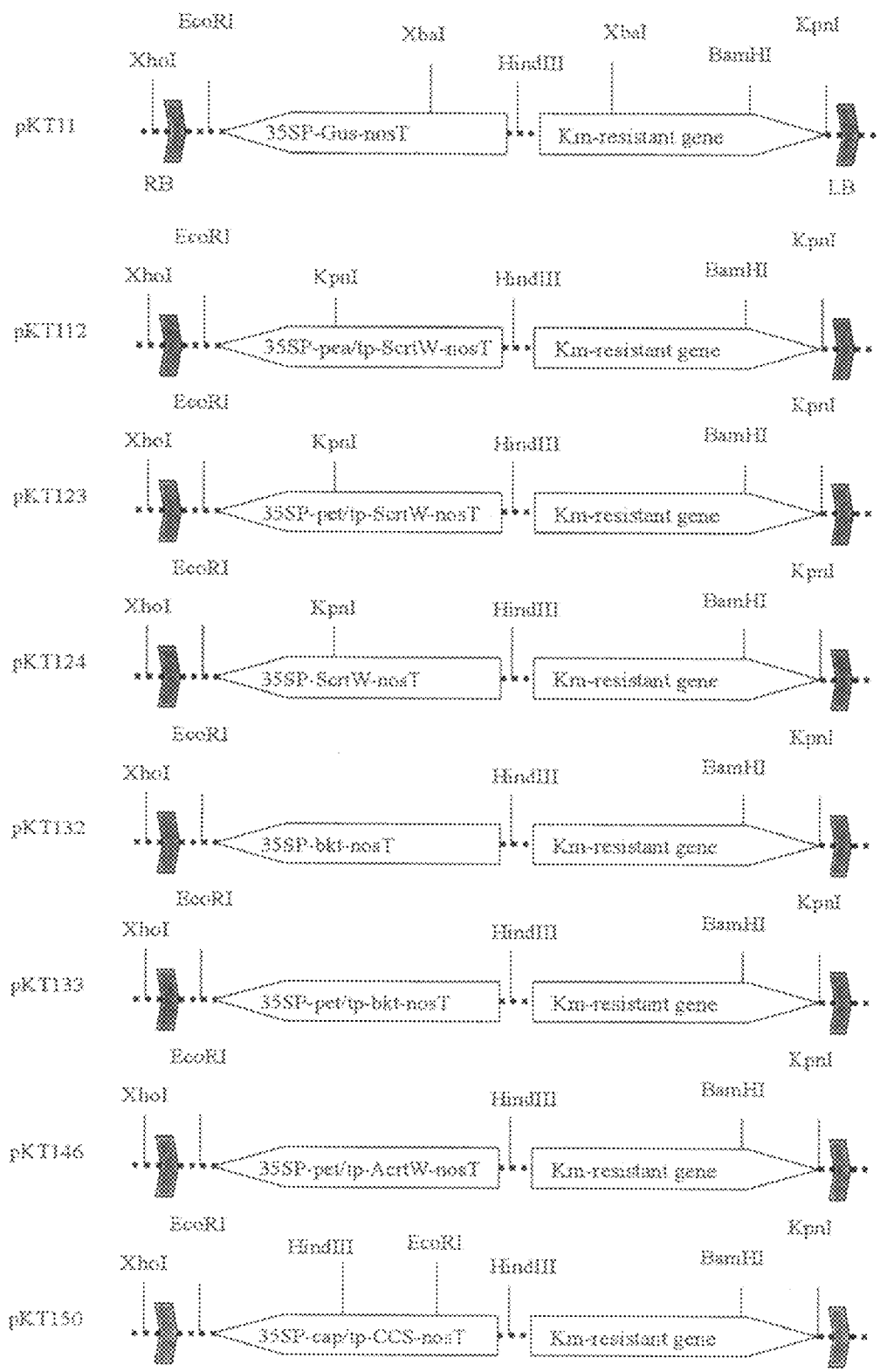
FIG. 2 shows structures of various types of vectors used for transformation.

The present invention is hereafter described in greater detail. This description includes part or all of the contents as disclosed in the description and/or drawings of Japanese Patent Application No. 2004-344059, which is a priority document of the present application filed on Nov. 29, 2004.

1. Transit Peptides and Genes Encoding the Same

The peptide of the present invention is a transit peptide having a function of transporting to chromoplasts in petals so as to cause the expression of a target protein that has been ligated to the peptide in chromoplasts in petals.

A novel transit peptide having such function, which has been found in accordance with the present invention, is a transit peptide of a petunia fibrillin gene, that of a capsanthin-capsorubin synthase gene of capsicum, or that of a cytokinin synthase gene of the *Agrobacterium*.

Specifically, the transit peptide of the present invention is: (a) a peptide consisting of the amino acid sequence set forth in SEQ ID NO: 2, 4, 30, 32, or 34; or (b) a peptide consisting of an amino acid sequence derived from the amino acid sequence set forth in SEQ ID NO: 2, 4, 30, 32, or 34 by deletion, substitution, insertion, or addition of one or several amino acids and having transport activity to chromoplasts in petals.

Further, in addition to such DNA sequence that exists in a plant gene sequence, a DNA sequence that exists in a gene sequence of another biological species or an artificially produced DNA sequence also can be used as the transit peptide of the present invention, as long as it has transport activity to chromoplasts in petals. The transit peptide of the present invention is described below in greater detail.

Regarding the above description "an amino acid sequence derived from the amino acid sequence set forth in SEQ ID NO: 2, 4, 30, 32, or 34 by deletion, substitution, insertion, or addition of one or several amino acids," the range indicated by the phrase "one or several" is not specifically defined. For instance, such phrase indicates approximately 1 to 20 amino acids, preferably 1 to 10 amino acids, more preferably 1 to 7 amino acids, further preferably 1 to 5 amino acids, and particularly preferably 1 to 3 amino acids.

Deletion, substitution, insertion, or addition of amino acids can be carried out by modifying a gene encoding the above peptide by techniques known in the art. Mutagenesis of such gene can be carried out by known methods such as the Kunkel method and the gapped duplex method and methods based on such methods. For instance, mutagenesis may be carried out using mutagenesis kits (e.g., Mutant-K (TAKARA) and Mutant-G (TAKARA)) to which a site-specific mutagenesis method has been applied or an LA PCR in vitro Mutagenesis series kit (TAKARA).

The above phrase "transport activity to chromoplasts in petals" indicates an activity of transporting exclusively to chromoplasts in petals in a specific and selective manner so as to cause the expression of a gene encoding a target protein that has been ligated (hereafter referred to as a "target gene") in chromoplasts in petals. The phrase "having transport activity to chromoplasts in petals" indicates that such activity is substantially equivalent to the activity of a peptide consisting of the amino acid sequence set forth in SEQ ID NO: 2, 4, 30, 32, or 34.

It is possible to confirm whether or not a mutant peptide as described above actually has transport activity to chromoplasts in petals in a manner whereby: vectors are produced by ligating various types of reporter genes, including genes of β-glucuronidase (GUS), luciferase (LUC), green fluorescent protein (GFP), chloramphenicol acetyl transferase (CAT), β-galactosidase (LacZ), nopaline synthase (NOS), and octopine synthase (OCS), to the downstream region of a gene encoding the above peptide; the vectors are inserted into plant cells in accordance with various forms of conventionally used transformation methods (described below); and the expression levels of the reporter genes are determined. Further, in accordance with the most effective method, a ketolase gene or a capsanthin-capsorubin synthase gene is used as a reporter gene in a petunia producing carotenoid, followed by measurement of changes in petal color development. Such measurement method can be applied to evaluation of not only such mutant peptide but also the original transit peptide thereof.

With the use of the method of the present invention, it is possible to readily determine whether or not a DNA sequence that exists in a plant gene sequence has transport activity to petals. In addition, it is also possible to determine whether or not a DNA sequence that exists in a gene sequence of another biological species or an artificially produced DNA sequence has such activity. Specifically, with the use of methods described below, for example, it is possible to identify a sequence, which does not originally function as a sequence of a transit peptide, as a transit peptide having transport activity to chromoplasts in petals. As examples of DNA sequences that exist in gene sequences of other biological species, sequences of yeasts are described below. All gene sequences of yeasts (Saccharomyces cerevisiae) have been determined [Goffeau et al., Science, 274, 546, 563-7 (1996)]. Nearly 6000 protein sequences have been predicted. The sequences are disclosed in the Saccharomyces Genome Database (http://www.yeastgenome.org/). Among such protein sequences, those possibly having transit peptide activity can be extracted by ChloroP [Emanuelsson et al., Protein Science, 8, 978-984 (1999)]. DNAs are selected from cultured yeasts. Then, a sequence possibly transit peptide activity is amplified by PCR using appropriate DNA primers. With the thus obtained DNA fragments, for example, cDNA encoding a transit peptide of a petunia fibrillin contained in pKT123 or cDNA encoding a transit peptide of a capsanthin-capsorubin synthase contained in pKT150 are replaced. Further, a vector used for plant transformation is produced, which is ligated to a gene encoding an enzyme protein involved in the carotenoid biosynthetic pathway, such as a ketolase gene and a capsanthin-capsorubin synthase gene. Thereafter, a transformed plant is produced in accordance with Example 6 described below. The obtained transformant is subjected to a test for evaluation of orange flower color in accordance with Example 7 described below, for example. Then, the plant is subjected to the measurement of changes in flower color development such that a sequence having transport activity to chromoplasts in petals can be adequately selected.

It has recently been reported that a cytokinin synthase gene (ipt gene) located on a Ti plasmid of a microorganism (Agrobacterium) localizes in stroma of a plastid (plastid) of a host plant cell, although it does not have a specific transit peptide [Abstracts of lectures in the 46$^{th}$ Annual Meeting of the Japanese Society of Plant Physiologists, p. 124; Abstracts of lectures in symposia of the 23$^{rd}$ Annual Meeting of the Japanese Society for Plant Cell and Molecular Biology (Kyoto, Japan), p. 19]. DNAs are extracted from cultured microorganisms (Agrobacterium). Then, a sequence possibly having transit peptide activity is amplified by PCR using appropriate DNA primers. With the thus obtained DNA fragments, for example, cDNA encoding a transit peptide of a petunia fibrillin contained in pKT123 or cDNA encoding a transit peptide of a capsanthin-capsorubin synthase contained in pKT150 are replaced. Further, a vector used for plant transformation is produced, which is ligated to a gene encoding an enzyme protein involved in the carotenoid biosynthetic pathway, such as a ketolase gene or a capsanthin-capsorubin synthase gene. Thereafter, a transformed plant is produced in accordance with Example 6 described below. The obtained transformant is subjected to a test for evaluation of orange flower color in accordance with Example 7 described below, for example. Then, the plant is subjected to measurement of changes in flower color development such that a sequence having transport activity to chromoplasts in petals can be adequately selected.

A gene encoding a transit peptide having the amino acid sequence set forth in SEQ ID NO: 2 of the present invention can be obtained by extracting mRNA from a petunia petal and carrying out reverse polymerase chain reaction (referred to as RT-PCR in some cases) with the use of such mRNA as a template, followed by amplification. In addition, a gene encoding a transit peptide having the amino acid sequence set forth in SEQ ID NO: 4 of the present invention can be obtained by obtaining genomic DNA from a capsicum and carrying out polymerase chain reaction (referred to as PCR in some cases), followed by amplification. Further, an ipt gene encoding a protein having an amino acid sequence set forth in SEQ ID NO: 30, 32, or 34 can be obtained by culturing a microorganism (the Agrobacterium), extracting genomic DNA, and carrying out PCR using such genomic DNA as a template, followed by amplification.

Specifically, the gene encoding a transit peptide of the present invention is a DNA consisting of the nucleotide sequence set forth in SEQ ID NO: 1, 3, 29, 31, or 33.

In addition, the gene encoding a transit peptide of the present invention involves a mutant gene. For instance, such gene may be DNA that hybridizes under stringent conditions to DNA consisting of a nucleotide sequence complementary to DNA consisting of the nucleotide sequence set forth in SEQ ID NO: 1, 3, 29, 31, or 33 and that encodes a peptide having transport activity to chromoplasts in petals.

Herein, the term "stringent conditions" indicates conditions under which a so-called specific hybrid is formed and a nonspecific hybrid is not formed. For instance, in the cases of such conditions, sodium concentration is 10 to 300 mM and preferably 20 to 100 mM and temperature is 25° C. to 70° C. and preferably 42° C. to 55° C.

Further, the gene encoding a transit peptide of the present invention involves DNA that consists of a nucleotide sequence at least 80%, preferably at least 90%, and the most preferably at least 95% homologous to the nucleotide sequence set forth in SEQ ID NO: 1, 3, 29, 31, or 33 and that encodes a peptide having transport activity to chromoplasts in petals. Herein, the numerical value in terms of homology is calculated on the basis of default (initial setting) parameters with the use of a nucleotide sequence comparison program such as DNASIS-Mac v. 3.7 (Hitachi Software Engineering Co., Ltd.) or GENETYX ver. 4.0 (GENETYX CORPORATION).

Furthermore, the above mutant gene (mutant DNA) can be produced in accordance with known methods such as the Kunkel method and the gapped duplex method or methods based on such methods with the use of, for example, mutagenesis kits (e.g., Mutant-K (TAKARA) and Mutant-G (TAKARA)) to which a site-specific mutagenesis method has been applied or an LA PCR in vitro Mutagenesis series kit (TAKARA). The above mutagenesis methods can be selected and carried out by persons skilled in the art without specific difficulties by referring to the nucleotide sequences of the genes according to references such as Molecular Cloning [edited by Sambrook et al., 15, Site-directed Mutagenesis of Cloned DNA, 15.3 to 15.113, Cold Spring Harbor Lab. Press, New York (1989)]. In addition, persons skilled in the art can implement a technique (site-specific mutagenesis) wherein substitution, deletion, insertion, or addition of one or more (one or several) base(s) is artificially carried out based on the nucleotide sequences of the genes, such technique being based upon a technique described in Proc. Natl. Acad. Sci. U.S.A., 81, 5662-5666 (1984); WO85/00817; Nature, 316, 601-605 (1985); Gene, 34, 315-323 (1985); Nucleic Acids Res., 13, 4431-4442 (1985); Proc. Natl. Acad. Sci. U.S.A., 79, 6409-6413 (1982); Science, 224, 1431-1433 (1984); or the like.

2. Target Genes

The target gene of the present invention, which imparts a yellowish color to petals, is not particularly limited as long as it is a gene encoding an enzyme protein involved in the carotenoid biosynthetic pathway. Herein, such yellowish color is expressed as color tone ranging from yellow through orange to red.

Examples of such gene encoding an enzyme protein involved in the carotenoid biosynthetic pathway that can be used include a β-caroteneketolase gene, an enzyme gene involved in the carotenoid compound synthesis that occurs upstream of the carotenoid biosynthetic pathway from FPP through GGPP to β-carotene, and a capsanthin-capsorubin synthase gene.

Herein, the term "β-caroteneketolase" (hereafter referred to as ketolase) indicates an enzyme that imparts a keto (oxo) group to a carbon atom at the 4-position of a β-ionone ring of carotenoid and is involved in the carotenoid compound synthesis downstream of the carotenoid biosynthetic pathway. Examples thereof include a canthaxanthin synthase and an astaxanthin synthase. In accordance with the present invention, specific examples of a ketolase gene that can be used include: the ScrtW gene (SEQ ID NO: 5), which encodes a protein identical to that encoded by a ketolase gene (crtW) of *Agrobacterium* and is modified so as to be used for a torula yeast (described in JP Patent No. 3375639); the AcrtW gene (SEQ ID NO: 6), which is a ketolase gene of *Alcaligenes* (also described in JP Patent No. 3375639); and the bkt gene (SEQ ID NO: 7), which is a ketolase gene of *Haematococcus pluvialis* (described in JP Patent No. 2960967). In particular, the ScrtW gene is preferable.

The ScrtW gene can be prepared with reference to the nucleotide sequence set forth in SEQ ID NO: 5 by synthesizing DNAs having appropriate lengths and ligating the resulting fragments. The AcrtW gene can be obtained by PCR using the genomic DNA of *Alcaligenes* sp. PC-1 as a template, followed by amplification. In addition, the bkt gene can be obtained by extracting mRNA of *Haematococcus pluvialis* and carrying out RT-PCR using such mRNA as a template, followed by amplification.

Examples of an enzyme involved in the carotenoid compound synthesis that occurs upstream of the carotenoid biosynthetic pathway from FPP through GGPP to β-carotene include a geranylgeranyl pyrophosphate (GGPP) synthase, a phytoene synthase, a lycopene synthase (phytoene desaturase), a β-cyclase, an isopentenyl diphosphate isomerase, a hydroxymethylglutaryl CoA (HMG-CoA) reductase, and a 1-deoxy-D-xylose-5-phosphate synthase. In accordance with the present invention, examples of such enzyme gene that can be used include: the GGPP synthase gene (crtE: SEQ ID NO: 8), which is derived from *Ervinia uredovora* (JP Patent No. 2950888); the phytoene synthase gene (crtB: SEQ ID NO: 9); the lycopene synthase gene (crtI: SEQ ID NO: 10); the β-cyclase gene (crtY: SEQ ID NO: 11); the isopentenyl diphosphate (IPP) isomerase gene (IDI1: SEQ ID NO: 12), which is derived from *Saccharomyces cerevisiae* (Anderson et al., J. Biol. Chem. 264, 19169-19175 (1989)); and the 1-deoxy-D-xylose-5-phosphate synthase gene (DXS: SEQ ID NO: 13), which is derived from *Escherichia coli* (Matthews and Wurtzel, Appl. Microbiol. Biotechnol., 53, 396-400 (2000)). In particular, the crtB gene is preferable. Each gene described above can be obtained by PCR using genomic DNA derived from the corresponding microorganism as a template, followed by amplification.

An example of a capsanthin-capsorubin synthase gene that can be used is the capsanthin-capsorubin synthase gene (CCS: SEQ ID NO: 14) of capsicum (Bouvier et al., Plant J., 6, 45-54 (1994)). The CCS gene can be obtained by extracting genomic DNA from capsicum and carrying out PCR, followed by amplification.

These genes encoding enzyme proteins involved in the carotenoid biosynthetic pathway are ligated to cDNA fragments encoding the transit peptides described in 1. above. Such genes encoding enzyme proteins involved in the carotenoid biosynthetic pathway may be used alone or in combinations of two or more. In addition, combinations of genes encoding transit peptides and genes encoding enzyme proteins involved in the carotenoid biosynthetic pathway are not particularly limited as long as the aforementioned genes are used. However, preferred examples of such combinations include a combination of a gene encoding a transit peptide of a petunia fibrillin gene and the ScrtW gene, that of a gene encoding a transit peptide of a petunia fibrillin gene and the CrtB gene, and that of a gene encoding a transit peptide of a cytokinin synthase gene of the *Agrobacterium* and the ScrtW gene. In addition, in the case of a capsanthin-capsorubin synthase gene of capsicum, a gene encoding a peptide portion having transit peptide activity is contained in the upstream region of such synthase gene. Thus, it is possible to use such gene without additionally combining it with a gene encoding a transit peptide. The combinations of such genes may be in the form of fused genes. Specific examples of a fused gene that can be used include a fused gene formed of a gene consisting of the nucleotide sequence set forth in SEQ ID NO: 1 and a gene consisting of the nucleotide sequence set forth in SEQ ID NO: 5, that of a gene consisting of the nucleotide sequence set forth in SEQ ID NO: 1 and a gene consisting of the nucleotide sequence set forth in SEQ ID NO: 9, that of a gene consisting of the nucleotide sequence set forth in SEQ ID NO: 3 and a gene consisting of the nucleotide sequence set forth in SEQ ID NO: 14, and that of a gene consisting of the nucleotide sequence set forth in SEQ ID NO: 29 and a gene consisting of the nucleotide sequence set forth in SEQ ID NO: 5.

Also, in addition to DNAs consisting of the above nucleotide sequences, examples of a gene encoding an enzyme protein involved in the carotenoid biosynthetic pathway include DNA consisting of a nucleotide sequence derived from such nucleotide sequence by deletion, substitution, insertion, or addition of one or several bases, DNA that hybridizes under stringent conditions to DNA consisting of a nucleotide sequence complementary to DNA consisting of such nucleotide sequence, and DNA consisting of a nucleotide sequence that is at least 80% homologous to such nucleotide sequence, as long as these examples retain their original enzyme activities.

3. Recombinant Vectors

The recombinant vector of the present invention can be constructed by introducing a fused gene, in which the target gene described in 2. above is ligated to the gene encoding a transit peptide described in 1. above, into an adequate vector. Herein, a preferred example of such vector that can be used is a vector derived from pBI, pPZP, or pSMA, with which a target gene can be introduced into a plant with the use of the *Agrobacterium*. In particular, a binary vector derived from pBI or an intermediate vector system is preferably used. Examples of such vector include pBI121, pBI101, pBI101.2, and pBI101.3. A binary vector is a shuttle vector that can be replicated in *Escherichia coli* and *Agrobacterium*. When a plant is caused to be infected with *Agrobacterium* carrying a binary vector, a partial DNA that is sandwiched by border sequences (an LB sequence and an RB sequence) located on a vector can be incorporated into a nuclear DNA of a plant [EMBO Journal, 10(3), 697-704 (1991)]. Meanwhile, in the case of a vector derived from pUC, a gene can be introduced directly into a plant. Examples of such vector include pUC18, pUC19, and pUC9. In addition, plant virus vectors such as a cauliflower mosaic virus (CaMV), a bean golden mosaic virus (BGMV), and a tobacco mosaic virus (TMV) vector can be used.

When a fused gene is inserted into a vector, a method wherein purified DNA is cleaved with an adequate restriction enzyme, the obtained DNA fragment is inserted into a restriction enzyme site or a multicloning site of an adequate vector DNA, and the resulting fused gene is ligated to a vector is used, for example.

It is necessary for the above fused gene to be incorporated into a vector in a manner such that functions of the gene are exerted. Thus, a vector may comprise constituents such as a promoter, an intron, an enhancer, a translation termination codon, a terminator, a polyA additional signal, a 5'-UTR sequence, and a selection marker gene in the upstream or downstream region of or inside of a fused gene. For such constituents, those known to the public may be used in combination according to need.

Examples of such promoter that may be used include a systemically-expressed promoter and a promoter that is known to function in a petal to result in a target gene being expressed in a petal. For instance, an example of such a systemically-expressed promoter is a cauliflower mosaic virus 35S promoter (35SP), and examples of such petal promoter include an EPSP synthase promoter and a chsA promoter of petunia. In addition, examples of a promoter that also may be used include: a promoter of an isopentenyl transferase (ipt) gene or a nopaline synthase (nos) gene of the *Agrobacterium*; a promoter derived from a promoter of a highly-expressed gene selected from a genome of a plant serving as a host used for transformation [Genschik et al., Gene, 148, 195-202 (1994)]; and a promoter exhibiting a very high level of promoter activity, selected from among chimeric promoters obtained by combining a plurality of the above promoters [Plant J., 7, 661-676 (1995)].

Note that promoters that can be used in the present invention are not limited to the above examples as long as the promoters are known to functions in petals. Further, such promoters can be obtained by an amplification reaction of PCR with the use of primers that are designed based on the nucleotide sequences of DNAs comprising such promoters and genomic DNA as a template. In such case, an example of template DNA that can be used for PCR is genomic DNA of a cauliflower mosaic virus.

In addition, if necessary, it is possible to introduce an intron sequence having a function of enhancing gene expression, such as an intron of corn alcohol dehydrogenase (Adh1) [Genes & Development, 1, 1183-1200 (1987)], between a promoter sequence and a gene.

Examples of an enhancer that can be used include a virus-derived translation enhancer and a plant-derived translation enhancer. Examples of such virus-derived translation enhancer include sequences of tobacco mosaic virus, Alfalfa mosaic virus RNA4, bromo mosaic virus RNA3, potato virus X, and tobacco H virus [Gallie et al., Nuc. Acids Res., 15, 8693-8711 (1987)]. In addition, examples of such plant-derived translation enhancer include a sequence derived from soybean β-1,3 glucanase (Glu) [written by Isao Ishida and Norihiko Misawa, edited by Kodansha Scientific, "Manuals for Cell Engineering Experimental Operations (*Saibo-Kogaku Jikken Sousa Nyumon*)," Kodansha Ltd., p. 119 (1992)] and a sequence derived from a tobacco ferredoxin-binding subunit (PsaDb) [Yamamoto et al., J. Biol. Chem., 270, 12466-12470 (1995)]. Examples of a translation termination codon include sequences of TAA, TAG, and TGA [e.g., Molecular Cloning described above].

As a terminator, a sequence capable of terminating transcription of a target gene transcribed by the aforementioned promoter may be used. Examples thereof include a terminator (nosT) of a nopaline synthase (nos) gene, a terminator of an octopine synthase (ocs) gene, and a terminator of a CaMV 35S RNA gene [Annu. Rev. Plant Physiol. Plant Mol. Biol., 44, 985-994 (1993); Plant Genetic Transformation and Gene Expression; a laboratory manual, edited by J. Draper et al., Blackwell Scientific Publication (1988)].

In addition, it has been reported that an enhancer region of a 35S gene was identified as a transcription enhancer inside of a promoter, and ligation of a plurality of such regions resulted in the improvement of the activity [Plant Cell, 1, 141-150 (1989)]. Such region also can be used as a part of a recombinant vector.

Examples of a selection marker gene include an ampicillin-resistant gene, a neomycin-resistant gene, a hygromycin-resistant gene, and a bialaphos-resistant gene. Further, a recombinant vector may be prepared by ligating such selection marker gene to a plasmid to which a target gene has been ligated in a manner similar to that described above. Alternatively, a recombinant vector obtained by ligating such selection marker gene to a plasmid and a recombinant vector obtained by ligating a target gene to a plasmid may be separately prepared. In such case, the obtained vectors may be cotransfected into a host.

Preferably, these various types of constituents are incorporated into a recombinant vector in a manner such that each constituent can function in accordance with its properties. Operations for such incorporation can adequately be carried out by persons skilled in the art.

4. Transformed Plants

With the use of the recombinant vector prepared in 3. above, it is possible to prepare a transformed plant by transforming cells of a plant of interest and regenerating such plant.

When a transformed plant is prepared, a variety of methods that have been reported and established can adequately be used. Preferred examples of such method for gene introduction include a biological method using a virus, or a Ti plasmid or an Ri plasmid of *Agrobacterium* as a vector and a physical method using electroporation, polyethylene glycol, particle gun, and microinjection [Plant Genetic Transformation and Gene Expression; a laboratory manual, edited by J. Draper et al., Blackwell Scientific Publication (1988)] or silicon nitride whiskers and silicon carbide whiskers [Euphytica, 85, 75-80 (1995); In Vitro Cell. Dev. Biol., 31, 101-104 (1995); and Plant Science, 132, 31-43 (1998)]. Such a method for gene introduction can adequately be selected and used by persons skilled in the art.

In general, a gene introduced into a plant is incorporated into the genome of a host plant. Upon such incorporation, a phenomenon referred to as a "position effect" is observed, in which the expression of a transgene varies depending on the position on the genome into which the transgene is introduced. Thus, it is necessary for a transgene to be confirmed.

It is possible to confirm whether or not a gene has been incorporated into a plant by PCR, Southern hybridization, Northern hybridization, Western blotting, or the like. For instance, DNA is prepared from a transformed plant and a DNA-specific primer is designed, followed by PCR. After PCR, an amplified product is subjected to agarose gel electrophoresis, polyacrylamide gel electrophoresis, capillary electrophoresis, or the like, followed by staining with ethidium bromide, an SYBR Green solution, or the like. Then, the completion of transformation can be confirmed by detecting an amplified product expressed in the form of a single band. In addition, it is also possible to perform PCR using a primer which has previously been stained with a fluorescent dye or the like so as to detect an amplified product. Moreover, a method wherein an amplified product is allowed to bind to a solid phase such as a microplate following which the amplified product is confirmed by a fluorescence or enzyme reaction or other means may be used.

In accordance with the present invention, examples of a plant to be transformed include: monocotyledons such as foliage plants of the families Liliaceae, Orchidaceae, and Araceae; and dicotyledons such as potatoes, chrysanthemums, roses, carnations, petunias, baby's breath, cyclamens, asters, salvias, and gentians. Cells of such plant can be used. Particularly preferred examples of plant types include: chrysanthemums, carnations, and roses, which are three major ornamental flowers in terms of production, distribution, and consumption throughout the world; and petunias, which have been increasingly produced, distributed, and consumed throughout the world in recent years.

In accordance with the present invention, examples of plant materials to be transformed include cells of growing points, shoot primordia, meristems, folia, stem pieces, root pieces, tuber pieces, petiol pieces, protoplasts, calluses, anthers, pollens, pollen tubes, peduncle pieces, flower stem pieces, petals, sepals, and the like.

In the cases of plant cells that are used for transformation, in order to regenerate a transformant from a transformed cell obtained, known tissue culture methods may be used. Persons skilled in the art can readily carry out operations for such regeneration with the use of methods of regenerating a plant from a plant cell that are known to the public. Regarding regeneration of a plant from a plant cell, it is possible to refer to references such as "Plant Cell Culture Manual (*Shokubutsu Saibo Baiyo Manual*)" [written and edited by Yasuyuki Yamada, Kodansha Scientific, 1984).

Specifically, a transformed plant cell is cultured in a medium used for callus formation, which is sterilized following the addition of mineral element, vitamins, carbon sources, sugars serving as energy sources, plant growth regulators (phytohormones such as auxin and cytokinin), and the like. Then, formation of a dedifferentiated callus that grows in an indefinite manner is induced (such induction being hereafter referred to as "callus induction"). The thus formed callus is transferred to a new medium containing plant growth regulators such as auxin, followed by further proliferation (subculture).

For instance, callus induction may be carried out using a solid medium made of agar or the like and subculture may be carried out in a liquid culture. In each such case, mass cultivation can be efficiently carried out. Next, a callus proliferated via the aforementioned subculture is cultured under adequate conditions, resulting in redifferentiation of organs (hereafter referred to as "induction of redifferentiation"). Eventually, a complete form of a plant is regenerated. The induction of redifferentiation can be carried out by adequately predetermining the types and amounts of constituents such as plant growth regulators (e.g., auxin and cytokinin) and carbon sources in a medium, lighting, temperatures, and the like. As a result of such induction of redifferentiation, adventitious embryos, adventitious roots, adventitious buds, adventitious stems and leaves, and the like are formed, leading to the growth of a further complete form. Alternatively, such plant at a state before it has reached its complete form (in the form of a capsulated artificial seed, a dried embryo, a lyophilized cell or tissue, or the like) may be preserved.

In addition, it is also possible to regenerate a transformant from a transformed plant cell without callus induction by adequately predetermining conditions related to the types and amounts of different constituents, lighting, temperatures, and the like.

The scope of the transformed plants of the present invention includes: plants of the "T1 generation" (redifferentiated generation as a result of transformation treatment; progeny plants of the "T2 generation" obtained using T1 seeds; progeny plants of the "T3 generation" (the next generation after T2 generation) obtained via self-pollination of flowers of "T2-generation" plants that are found to be transgenic plants via drug screening, a Southern analysis method, or the like; and individuals obtained via proliferation and maintenance of T1-generation plants with the use of clones.

5. Test for Evaluation of Flower Color

The flower color of a transformed plant can be evaluated by comparing the flower color upon flowering with the JHS color chart (edited by the Ministry of Agriculture, Forestry and Fisheries of Japan, published by the Japan Color Research Institute) and by carrying out chromaticity measurement of flower color upon flowering based on the L*a*b* color system (Japanese Industrial Standards: JIS Z 8729) with the use of a color difference meter. For instance, a test for evaluation of petunia flower color may be carried out as follows. Petals of 3 individuals from each line, which have fully opened after flowering, are subjected to the measurement of chromaticity 3 times with the use of a handy spectrophotometer (NF333; Nippon Denshoku). Then, the average of the values is calculated.

BEST MODE FOR CARRYING OUT THE INVENTION

The present invention is hereafter described with reference to the following examples, although the technical scope of the present invention is not limited thereto.

In addition, in vitro seedlings of "a light yellowish petunia (a breeding line of Kirin Beer Kabushiki Kaisha)" used in Examples described below have been preserved at the Shokubutsu Kaihatsu Kenkyusho; Kirin Beer Kabushiki Kaisha). Thus, they are available as experimental materials upon requests (address: 3377, Aza-Saruzuka, Saotome, Sakurashi, Tochigi 329-1414, Japan; telephone: 81 (country code)-28-686-0501; FAX: 81 (country code)-28-686-5060).

Example 1

Obtaining cDNA of Petunia Fibrillin

An in vitro petunia seedling (*Petunia hybrida*: light yellowish petunia (a breeding line of Kirin Beer Kabushiki Kaisha)) was acclimatized to culture soil (composition: Akadama (small): leaf mold: vermiculite=6:3:1) and cultivated according to a conventional method, leading to flowering. Preparation of mRNA from a petal was carried out using RNeasy kits (Qiagen). Synthesis of total cDNA was carried out using a SuperScript First-Strand Synthesis System (Invitrogen).

The resulting cDNA was subjected to PCR (conditions: 95° C. for 5 minutes; 95° C. for 30 seconds, 55° C. for 30 seconds, and 72° C. for 1 minute for 30 cycles; and 72° C. for 10 minutes) with the use of primers [Fib5-1: CAGCTGGAATC-CAAGAACCCTA (SEQ ID NO: 15) and Fib3-1: GTAAGTGGTCAGCAGCCATGAT (SEQ ID NO: 16)] that had been produced based on reference information regarding the capsicum fibrin gene [Deruere et al., Plant Cell, 6, 119-133 (1994)] and the cucumber fibrin gene [Vishnevetsky et al., Plant J., 10, 1111-1118 (1996)]. As PCR enzyme, ExTaq (Takara Shuzo Co., Ltd.) that was also used in the following experiments. The amplified product thereof was separated by 1% agarose gel electrophoresis at 100 V for 20 minutes, followed by visualization via ethidium bromide staining. DNA fragment having predicted molecular weights (corresponding to approximately 500 bases) was found to be amplified. The obtained amplified product was subjected to TA cloning ["Notes for PCR experiments (PCR Jikken Note)," written and edited by Taketoshi Taniguchi, YODOSHA Co., Ltd. (1997)] with the use of a pGEM T vector (Promega), followed by nucleotide sequencing with the use of ABI310 (Applied Biosystems). The resulting nucleotide sequence was translated into an amino acid sequence. As a result of examination of homology, the amino acid sequence was confirmed to be a partial sequence of petunia fibrillin cDNA. With the use of the thus obtained partial fibrillin sequence, a petunia cDNA library that had been produced from the total RNA with the use of a ZAP-cDNA™ Library Construction Kit (Stratagene) was screened for by a hybridization method. Accordingly, clone PetCarP4 comprising full-length cDNA of a fibrillin that functions in petunia petals was obtained. The clone was subjected to nucleotide sequencing with the use of ABI310.

Example 2

Obtaining Transit Peptide cDNA of Petunia Fibrillin

It was noticed that an amino acid sequence of a transit peptide predicted from the cDNA sequence of petunia fibrillin has no homology to an amino acid sequence of a transit peptide of *Pisum sativum*, such transit peptide being the most widely used as a transit peptide of a chloroplast [Schreier et al., EMBO J., 4, 25-32 (1985)]. Such fact was considered to be related to information regarding efficient transport of proteins to chromoplasts (FIG. 1).

Thus, PCR (conditions: 95° C. for 5 minutes; 95° C. for 30 seconds, 55° C. for 30 seconds, and 72° C. for 1 minute for 30 cycles; and 72° C. for 10 minutes) was carried out using DNA of the clone PetCarP4 as a template and primers [U383: ACTAGTACGGCTTTTACTGTGACTCTTG (SEQ ID NO: 17) and U384: TCTAGATTCTTCACTCATTTCCTCTC (SEQ ID NO: 18)]. The PCR product was subjected to TA cloning with the use of a pCR4-TOPO vector (Invitrogen) such that plasmid pTP1 was obtained, followed by nucleotide sequencing. The determined nucleotide sequence is set forth in SEQ ID NO: 1. In addition, an amino acid sequence encoded by the nucleotide sequence is set forth in SEQ ID NO: 2.

Example 3

Production of Vectors for Plant Transformation with the Use of Ketolase Genes

As the ketolase genes, the ScrtW gene (SEQ ID NO: 5) obtained by modifying crtW (a ketolase gene of *Agrobacterium*) for a torula yeast, the ketolase gene of *Alcaligenes* sp. PC-1 (AcrtW gene: SEQ ID NO: 6), and the ketolase gene of *Haematococcus pluvialis* (bkt gene: SEQ ID NO: 7), each of which were reported by Miura et al. [Appl. Environ. Microbiol., 64, 1226-9 (1998)], were used.

A plasmid p35SP-pt/tp-ScrtW comprising an expression cassette construct in which a 35S promoter (35SP), cDNA of fibrillin transit peptide, ScrtW, and a nos terminator (nosT) were aligned in such order was obtained by ligating cDNA of a transit peptide (pt/tp) of petunia fibrillin, which had been cleaved from pTP1 with XbaI and SpeI, to an XbaI site located between a 35S promoter and ScrtW of a plasmid p35SP-ScrtW containing a construct comprising a cauliflower mosaic virus 35S promoter (35SP), ScrtW, and a nos terminator (nosT). With the use of pKT11, which is a binary vector capable of being amplified with the *Agrobacterium* and *Escherichia coli* (JP Patent Publication (Kokai) No. 2001-161373 A), as a basic vector, pKT123 was constructed by replacing a Gus gene region of such vector with pet/tp-ScrtW cDNA of the above expression vector. In addition, a plasmid (pKT124) lacking cDNA of a transit peptide and a plasmid (pKT112) having a transit peptide (pea/tp) derived from the RubisCO gene of *Pisum sativum* [Schreier et al., EMBO J., 4, 25-32 (1985)] instead of a transit peptide (pet/tp) of fibrillin were produced.

Likewise, a plasmid (pKT133) in which the bkt gene (SEQ ID NO: 7) instead of ScrtW had been ligated to cDNA of a transit peptide of petunia fibrillin and a plasmid (pKT146) in which the AcrtW gene (SEQ ID NO: 6) instead of ScrtW had been ligated to the same were produced (FIG. 2).

Example 4

Figure 3:
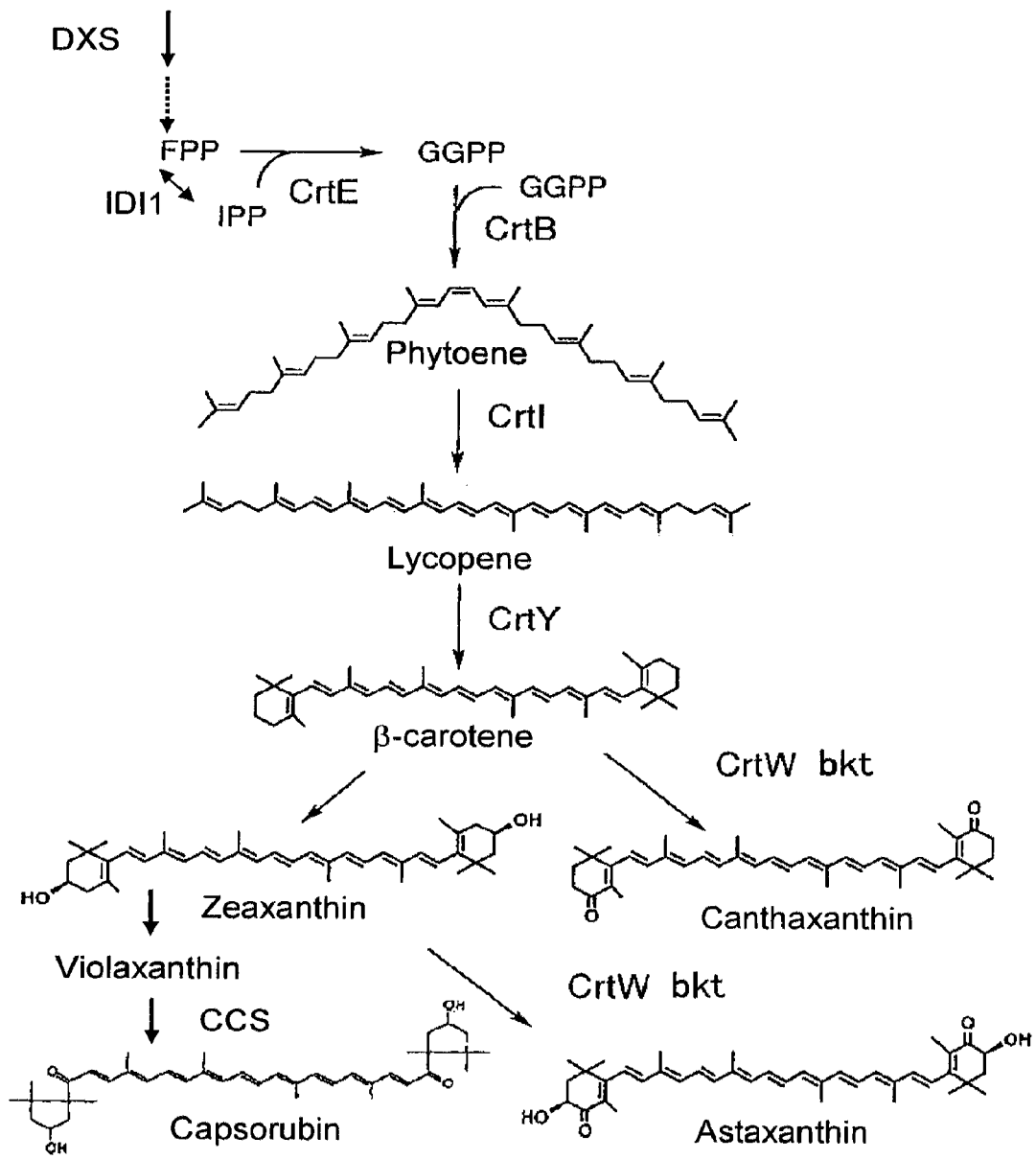
FIG. 3 shows the carotenoid biosynthetic pathway and genes involved in the biosynthetic pathway (DXS: 1-deoxy-D-xylose-5-phosphate synthase gene; IDI1: isopentenyl diphosphate (IPP) isomerase gene; crtE: GGPP synthase gene; crtB: phytoene synthase gene; crtI: lycopene synthase gene; crtY: β-cyclase gene; crtW: a ketolase gene common in the *Agrobacterium* and the *Alcaligenes*; bkt: a ketolase gene of *Haematococcus pluvialis*; and CCS: a capsanthin-capsorubin synthase gene).

Production of Vectors for Plant Transformation with the Use of Genes Involved in the Carotenoid Compound Synthesis that Occurs Upstream of the Carotenoid Biosynthetic Pathway In the carotenoid biosynthetic pathway (FIG. 3), various types of enzyme genes are involved in the carotenoid compound synthesis that occurs upstream of the carotenoid biosynthetic pathway from FPP through GGPP to β-carotene. The enzyme genes used were the crtE gene (SEQ ID NO: 8), the crtB gene (SEQ ID NO: 9), the crtI gene (SEQ ID NO: 10), the crtY gene (SEQ ID NO: 11), the IDI1 gene (SEQ ID NO: 12), and the DXS gene (SEQ ID NO: 13).

With the use of pKT123 of Example 3 as a basic vector, vectors for plant transformation (such vectors being referred to as pKT138, pKT139, pKT140, pKT141, and pKT149, respectively) were constructed by replacing the ScrtW gene with the crtI gene (SEQ ID NO: 10), the crtB gene (SEQ ID NO: 9), the crtE gene (SEQ ID NO: 8), the IDI1 gene (SEQ ID NO: 12), and the crtY gene (SEQ ID NO: 11).

In addition, the expression vector (p35SP-DXS) for the DXS gene (SEQ ID NO: 13) was provided by Dr. Fraser of the University of London.

Example 5

Production of Vectors for Plant Transformation with the Use of Capsanthin-Capsorubin Synthetic Genes Genomic DNA was obtained from a commercially available capsicum (Nikko Togarashi) with the use of DNeasy kits (Qiagen). PCR (conditions: 95° C. for 5 minutes; 95° C. for 30 seconds, 55° C. for 30 seconds, and 72° C. for 1 minute for 30 cycles; and 72° C. for 10 minutes) was carried out using the genomic DNA as a template and primers [U423: AGATCTTTCAAAGGCTCTCTATTGCTAGAT (SEQ ID NO: 19) and U424: ACTAGTTTTTTTCACTATACTATAT- CACC(SEQ ID NO: 20)] in order to obtain a gene fragment comprising a 5' untranslated region and a transit peptide. The PCR product was subjected to TA cloning with the use of a pCR4-TOPO vector (Invitrogen) such that a plasmid pTO-POCCS was obtained, followed by nucleotide sequencing. The nucleotide sequence was completely consistent with the nucleotide sequence (SEQ ID NO: 14) described in the existing report [Bouvier et al., Plant J., 6, 45-54 (1994)]. The amino acid sequence of the region functioning as a transit peptide predicted by ChloroP [Emanuelsson et al., Protein Science, 8, 978-984 (1999)] is set forth in SEQ ID NO: 4. In addition, the nucleotide sequence encoding such peptide is set forth in SEQ ID NO: 3 (corresponding to the nucleotide sequence between position 1 and position 117 of SEQ ID NO: 14).

With the use of pKT123 of Example 3 as a basic vector, pKT150 was constructed by replacing the pet/tp-ScrtW gene with a cap/tp-CCS gene (FIG. 2).

Example 6

Production of Transformed Petunia Plants

Each of the vectors produced in Examples 3, 4, and 5 was introduced into an *Agrobacterium tumefaciens* AGL0 strain by the electroporation method (Plant Molecular Biology Manual, edited by Gelvin and Schilperoor, C2, 1-32 (1994), Kluwer Academic Publishers). Each *Agrobacterium tumefaciens* AGL0 strain having a different vector was subjected to shake culture at 28° C. for 12 hours in a YEB liquid medium [5 g/l beef extract, 1 g/l yeast extract, 5 g/l peptone, 5 g/l sucrose, and 2 mM magnesium sulfate (pH7.2)] containing 50 ppm kanamycin. Each culture solution obtained (1.5 ml) was centrifuged at 10,000 rpm for 3 minutes, followed by cell harvesting. Then, the cells were washed with 1 ml of a LB medium for removal of kanamycin, followed by another centrifugation at 10,000 rpm for 3 minutes. The cells were harvested and resuspended in 1.5 ml of a YEB medium. Thus, obtained cell suspensions were used for infection.

Young leaves were collected from an aseptic light yellowish petunia plant (a breeding line of Kirin Beer Kabushiki Kaisha) and designated as leaves for *Agrobacterium* infection. The leaves were aseptically cut into 0.5- to 1-cm pieces with the use of a scalpel. The leaves were placed face down on each *Agrobacterium* cell suspension and lightly shaken for 5 minutes. Then, the leaves were placed on sterilized filter paper for removal of excessive *Agrobacterium* cells. A Whatman No. 1 filter paper (diameter (Φ): 7.0 cm) was placed on an MS medium (containing 1.0 ppm benzyladenine, 0.1 ppm indolebutyric acid, and 0.8% agar) [Murashige & Skoog, Physiol. Plant., 15, 473-497 (1962)] contained in a petri dish. The leaves were placed face down on the filter paper. The petri dish was sealed with Parafilm, followed by culture under conditions of 25° C., lighting for 16 hours (photon flux density: 32 μE/m$^2$s), and no lighting for 8 hours. Subsequently, the leaves were transferred onto a ½ MS medium containing 100 ppm kanamycin, 250 ppm Claforan, 0.3 ppm benzyladenine, and 0.1 ppm naphthaleneacetic acid. During such step, callus formation was observed in peripheral parts of the leaf pieces, resulting in generation of shoot primordia. After another culture, extended shoots were placed on an MS medium containing 250 ppm Claforan and 100 ppm kanamycin but not containing a plant growth regulator. Rooted shoots were detected by PCR of an individual containing a kanamycin-resistant gene (NPTII) serving as a foreign gene, such individual being selected from among grown plants resistant to kanamycin. Thus, the redifferentiated plants were confirmed to be transformants. Herein, TAAAGCACGAG-GAAGCGGT (SEQ ID NO: 21) and GCACAACAGA-CAATCGGCT (SEQ ID NO: 22) were employed as primers used for specific amplification of a sequence peculiar to the NPTII gene. PCR was carried out under reaction conditions of heating at 94° C. for 5 minutes, 30 cycles of 94° C. (30 seconds), 55° C. (1 minute), and 72° C. (1 minute), and a reaction at 72° C. for 10 minutes. For the reaction, Taq polymerase (Takara Shuzo Co., Ltd.) was used as an enzyme.

Accordingly, 13 types of petunia plants into which vectors (pKT112, pKT123, pKT124, pKT132, pKT133, pKT146, pKT150, pKT138, pKT139, pKT140, pKT141, pKT149, and p35SP-DXS) containing different genes had been separately introduced were obtained (66, 75, 54, 37, 46, 38, 39, 47, 52, 36, 35, 32, and 37 individuals, respectively).

Example 7

Test for Evaluation of Orange Flower Color

All individuals of transformed petunias that had been separately transformed with vectors (pKT112, pKT123, pKT124, pKT132, pKT133, pKT146, and pKT150), which were selected from among various types of transformed petunias obtained in Example 6, and 10 individuals of a nontransformant petunia (*Petunia hybrida*: light yellowish petunia (a breeding line of Kirin Beer Kabushiki Kaisha)) were each placed in a pot (diameter: 9 cm) accommodating culture soil (composition:red Akadama (small):leaf mold:vermiculite=6: 3:1), followed by cultivation according to a conventional method. Then, flowering was induced in a biohazard greenhouse. The flower color of a transformed petunia was evaluated by comparing the flower color upon flowering with the JHS color chart (edited by the Ministry of Agriculture, Forestry and Fisheries of Japan, published by the Japan Color Research Institute) and by carrying out chromaticity measurement of the flower color upon flowering based on the L*a*b* color system (Japanese Industrial Standards: JIS Z 8729). Chromaticity measurement based on the L*a*b* color system (Japanese Industrial Standards: JIS Z 8729) was carried out as follows. 3 petals of each individual from each line (provided that petals of all the individuals of the transformed petunias had fully opened after flowering) were subjected to the measurement of chromaticity 3 times with the use of a handy spectrophotometer (NF333; Nippon Denshoku). Then, the average of the values was calculated. The results relative to those obtained from the nontransformants were classified into different levels on the basis of color difference ΔE (Japanese Industrial Standards: JIS Z 8730) of the L*a*b*color system. The number of bloomed flowers at each level was obtained. The levels are expressed as follows:

−: no change in color tone (ΔE<5);

+: light orange color (5≦ΔE<20);

++: orange color (20≦ΔE<35); and

+++: deep orange color (35≦ΔE).

Table 1 shows occurrence rates of individuals having orange flower colors among from plants transformed with different vectors.

TABLE 1

Occurrence rates of individuals having orange flower colors among from transformants transformed with different vectors

| Vector | tp | Transgene | Number of bloomed individuals | Orange-colored individuals relative to bloomed individuals | Orange-colored individuals relative to bloomed individuals (at each level) | | | | | | | |
|---|---|---|---|---|---|---|---|---|---|---|---|---|
| | | | | | +++ | (%) | ++ | (%) | + | (%) | − | (%) |
| No vector | — | — | 10 | 0 | 0% | 0 | 0% | 0 | 0% | 0 | 0% | 10 | 100% |
| pKT112 | pea/tp | ScrtW | 66 | 29 | 44% | 6 | 9% | 19 | 29% | 4 | 6% | 37 | 56% |
| pKT123 | pea/tp | ScrtW | 75 | 49 | 65% | 14 | 19% | 19 | 25% | 16 | 21% | 26 | 35% |
| pKT124 | — | ScrtW | 54 | 0 | 0% | 0 | 0% | 0 | 0% | 0 | 0% | 54 | 100% |
| pKT132 | — | bkt | 37 | 0 | 0% | 0 | 0% | 0 | 0% | 0 | 0% | 37 | 100% |
| pKT133 | pea/tp | bkt | 46 | 21 | 46% | 3 | 7% | 5 | 11% | 13 | 28% | 25 | 54% |
| pKT146 | pea/tp | AcrtW | 38 | 30 | 79% | 2 | 5% | 15 | 39% | 13 | 34% | 8 | 21% |
| pKT150 | cap/tp | CCS | 39 | 26 | 67% | 1 | 3% | 12 | 31% | 13 | 33% | 13 | 33% |

Individuals that had been transformed with pKT123 (transit peptide: pet/tp; transgene: ScrtW) had petals having orange colors. In addition, the number of such individuals that had deep orange colors was greater than that of individuals transformed with pKT112 (transit peptide: pea/tp, transgene: ScrtW). That is, the results show that the percentage of orange-colored individuals evaluated at the highest level (+++) in bloomed individuals in the case of pKT123 was higher compared with the case of pKT112. In addition, the deepest flower color (+++) derived from pKT123 was deeper than the deepest flower color derived from pKT112. According to the JHS color chart, the color of a tube part (floral tube) of a nontransformant was 7Y-2706 (strong greenish yellow), while on the other hand, the color of that part of the individual no. 33 obtained via transformation with pKT123 was 3YR-1307 (deep orange) (FIG. 4).

Herein, codes such as 7Y-2706 and 3YR-1307 are alternative means for describing the observed color phenotypes. Thus, such codes should be regarded as indices of observed colors. Therefore, potential colors that can be obtained in accordance with the present invention are not limited thereto. In addition, in terms of numerical values of the xyz color system included in the color chart, 7Y-2706 is expressed as L*=81.35, a*=−9.68, and b*=94.00, and 3YR-1307 is expressed as L*=56.66, a*=37.49, and b*=63.59 according to the L*a*b*color system.

Also, the expression of orange color was confirmed in 46% of transformants transformed with pKT133 (transit peptide: pet/tp; transgene:bkt) and 79% of transformants transformed with pKT146 (transit peptide:pet/tp; transgene:AcrtW). Further, large numbers of orange-colored individuals among bloomed individuals were obtained also in the cases of transformants transformed with pKT150 (transit peptide:ccs/tp; transgene:CCS).

Table 2 shows results of comparison in terms of petal color. For such comparison, the color expressed in a single petal of each individual (3 individuals (line nos.: 5, 65, and 67) selected from among 14 individuals transformed with pKT123, each individual being evaluated at the level "+++") was directly measured using a handy spectrophotometer (NF333). Then, the results were compared with those obtained from a nontransformant (1 individual). Measurement was carried out 3 times. Thereafter, the average of the obtained numerical values was calculated. Note that such color measurement is an alternative means for describing observed color phenotypes. Thus, such codes should be regarded as indices of observed colors. Therefore, potential colors that can be obtained in accordance with the present invention are not limited thereto.

TABLE 2

Colors expressed in pKT123 transformants

| Line no. | L* | a* | b* | ΔE |
|---|---|---|---|---|
| Nontransformant | 71.05 | −11.27 | 81.49 | |
| 5 | 62.24 | 21.29 | 65.07 | 37.52 |
| 65 | 63.01 | 20.57 | 62.20 | 38.08 |
| 67 | 59.75 | 18.63 | 62.85 | 37.00 |

Accordingly, in a case in which the transit peptide (pet/tp) of petunia fibrin of the present invention was used instead of a transit peptide (pea/tp) of the RubisCO gene of *Pisum sativum*, which has been the most widely used, the large number of individuals expressing the orange color was obtained in combination with any ketolase enzyme gene. In particular, it was found that a significant effect of the use of the transit peptide of the present invention can be obtained when the transit peptide is used in combination with the ScrtW gene.

In addition, similar effects were obtained in the case of the capsanthin-capsorubin synthase gene (CCS gene). Thus, it has been shown that the structure of a petunia petal is analogous to the structure of a chromoplast of a capsicum fruit so that a transit peptide functioning in a transit peptide of a capsicum fruit also can function in a chromoplast in a petunia petal.

Example 8

Test for Evaluation of Yellow Flower Color

From among various types of petunia transformants obtained in Example 6, transformants transformed with different vectors (pKT138, pKT139, pKT140, pKT141, pKT149, and p35SP-DXS) into each of which a different upstream gene in the pathway to β-carotene had been incorporated were selected (47, 52, 36, 35, 32, and 37 individuals, respectively). The individuals were cultivated as with the case of Example 7. After flowering, a test for evaluation of flower color was carried out. Changes in color tone (relative to those obtained from nontransformants) were evaluated on the basis of color difference ΔE of the L*a*b*color system as follows:

−: no change in color tone (ΔE<5);

+: light orange color (5≦ΔE<10); and

++: orange color (10≦ΔE).
In addition, the areas of regions in which color tone change had been observed were evaluated as follows:
  −: no change in color tone (change in area<10%);
  +: slightly enlarged (10%≦change in area<50%);
  ++: significantly enlarged (50%≦change in area).
Table 3 lists the results.

TABLE 3

Conditions of yellow petals of transformants transformed with different vectors

| Vector | Transgene | Depth of yellow color | Enlargement of the yellow region |
|---|---|---|---|
| Nontransformant | — | − | − |
| pKT138 | crtI | + | + |
| pKT139 | crtB | ++ | ++ |
| PKT140 | crtE | + | + |
| pKT141 | IDI1 | + | + |
| pKT149 | crtY | + | + |
| p35SP-DXS | DXS | + | + |

Figure 5:
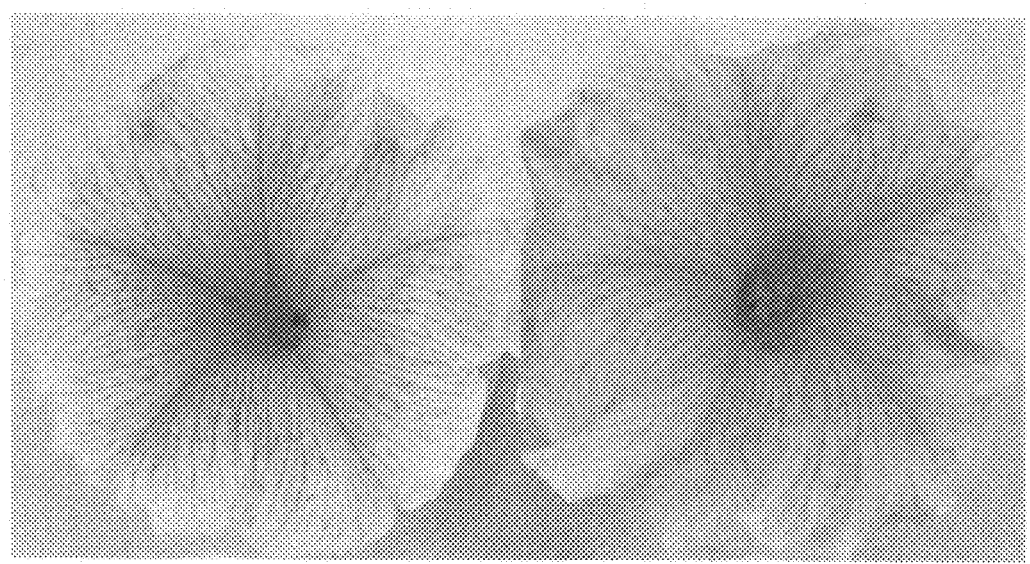
FIG. 5 shows an image for comparison of petals of a transformant transformed with pKT139 and those of a nontransformant.

It has been shown that pKT139, which is a phytoene synthase, has the strongest effects of causing depth of yellow color and enlargement of the yellow region. FIG. 5 shows an image of petals of a transformant transformed with pKT139 and those of a nontransformant.

Table 4 shows results of comparison in terms of petal color. For such comparison, the color expressed in a single petal of each individual (3 individuals (line nos.: 10, 20, and 23) selected from among 13 individuals transformed with pKT123, each individual being evaluated at the level "++") was directly measured using a handy spectrophotometer (NF333). Then, the results were compared with those obtained from a nontransformant (1 individual). Measurement was carried out 3 times. Thereafter, the average of the obtained numerical values was calculated. Note that such color measurement is an alternative means for describing observed color phenotypes. Thus, such codes should be regarded as indices of observed colors. Therefore, potential colors that can be obtained in accordance with the present invention are not limited thereto.

TABLE 4

Petal colors expressed in pKT139 transformants

| Line no. | L* | a* | b* | ΔE |
|---|---|---|---|---|
| Nontransformant | 71.05 | −11.27 | 81.49 | |
| 10 | 62.18 | −3.16 | 68.73 | 17.52 |
| 20 | 70.28 | −1.61 | 75.43 | 11.42 |
| 23 | 70.31 | 2.12 | 79.57 | 13.55 |

Example 9

Extraction of Protein Sequences Each Possibly Having Transit Peptide Activity Predicted from Yeast Genome Sequences Sequences each possibly having transit peptide activity were extracted by the method of ChloroP [Emanuelsson et al., Protein Science, 8, 978-984 (1999)] with reference to protein sequences disclosed in *Saccharomyces* Genome Database (http://www.yeastgenome.org/). As a result, 721 types of sequences were extracted relative to 5872 types of expected protein sequences. Considering the length of a transit peptide of petunia fibrillin (59 amino acids) and that of a transit peptide of capsanthin-capsorubin synthase (39 amino acids), transit peptides of interest were predicted to have amino acid sequences comprising 35 to 65 amino acids. Further, 385 types of sequences were extracted from the above sequences. Furthermore, 46 types of sequences were eventually obtained, such sequences having, as indices, scores exceeding the score of petunia fibrillin (0.563).

ORF codes serving as reading frames of the proteins are listed below. YMR122W-A, YOL148C, YLR310C, YCL027W, YER093C, YER069W, YML016C, YPL253C, YDR077W, YGL092W, YDR097C, YHR116W, YJL095W, YDR159W, YNL288W, YGR119C, YMR075W, YDR524C-B, YCR008W, YNL154C, YER088C, YLR187W, YPL137C, YLL029W, YOR162C, YNL169C, YDR006C, YDR538W, YML059C, YNL197C, YNL271C, YPL159C, YKL141W, YLR144C, YDR223W, YJR144W, YOR232W, YHR031C, YER167W, YLR332W, YPL242C, YPR019W, YOR098C, YOR247W, YHL033C, and UJR138W A strain of the yeast (*Saccharomyces cerevisae*) S288C (IFO 1136) was cultured in a medium (composition: 2% tripton; 1% yeast extract; and 2% glucose) in accordance with a conventional method, followed by DNA extraction with the use of GenTLE™ (Takara Bio Inc.);

Example 10

Production of Vectors Used for Examination of a Transit Peptide of a Capsanthin-Capsorubin Synthase Gene The following oligonucleotide primers were synthesized, followed by PCR using DNA of pKT 150 as a template.

5'-CATATGGAAACCCTTCTAAAGCC-3'    (SEQ ID NO: 23)

5'-ACTAGTAACTTTCTTGAATCTTTTTG-3'    (SEQ ID NO: 24)

Figure 6:
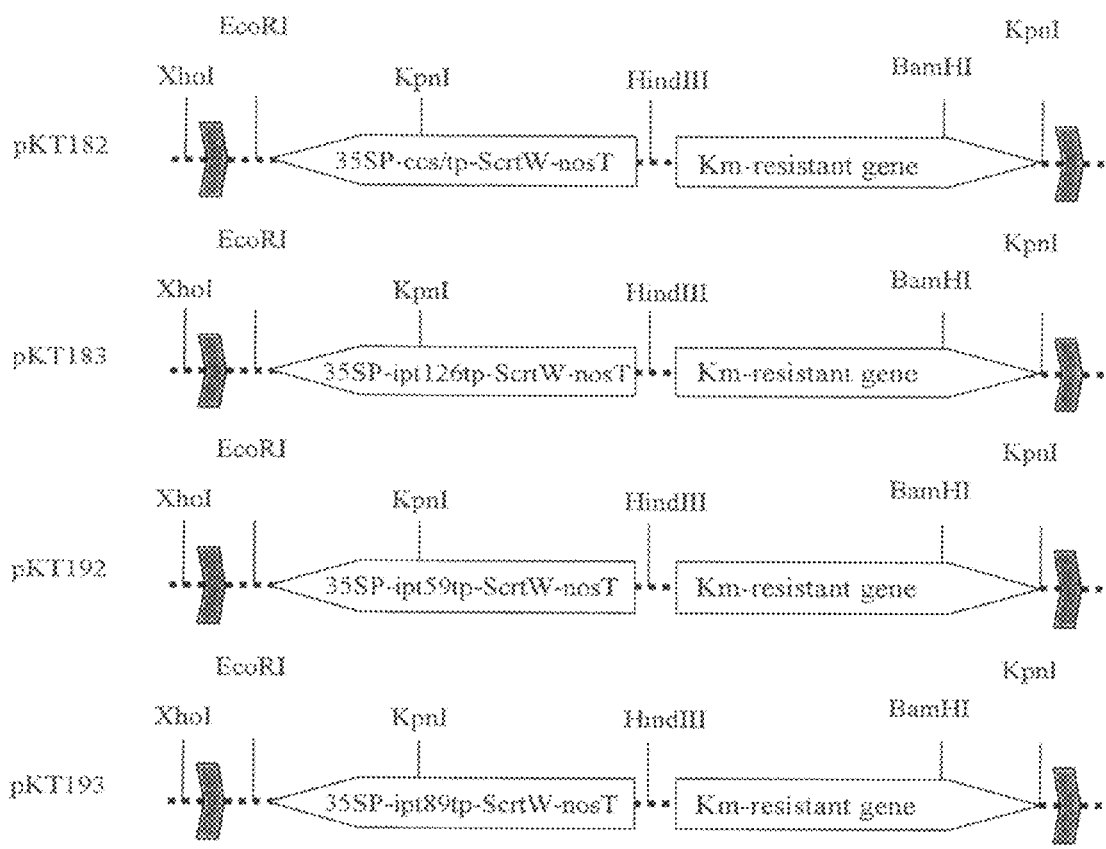
FIG. 6 shows structures of vectors used for transformation, each vector comprising the ipt gene.

The amplified DNA (ccs/tp) was first cloned into a vector with the use of a TOPOTA cloning kit (Invitrogen). Then, the nucleotide sequence thereof was confirmed using ABI310. With the use of pKT123 of Example 3 as a basic vector, pKT182 was constructed by replacing pet/tp with ccs/tp (FIG. 6). Three types of petunia plants into each of which a vector (pKT182) comprising the ccs/tp gene had been introduced were obtained (37 individuals each) by the method of Example 6.

Example 11

Production of Vectors for Examination of a Transit Peptide of the *Agrobacterium* Cytokinin Synthase Gene The ipt gene sequence of a Ti plasmid in an *Agrobacterium tumefaciens* A281 strain has been registered with DDBJ (ACCESSION No. X14410). The following oligonucleotide primers were synthesized, followed by PCR using total DNA (JP Patent Publication (Kokai) No. 11-69979 A (1999)) as a template, such total DNA being extracted from cells of the *Agrobacterium tumefaciens* A281 strain.

```
Primer A1:
5'-CATATGGATCTACGTCTAATTTT-3'         (SEQ ID NO: 25)

Primer A2:
5'-ACTAGTGCTAACTCGTTGCGAATAA-3'       (SEQ ID NO: 26)

Primer A3:
5'-ACTAGTAGACGAGTCGTTCCTTTCAG-3'      (SEQ ID NO: 27)

Primer A4:
5'-ACTAGTTTGGCCTCGTGATTGTGCAC-3'      (SEQ ID NO: 28)
```

PCR was carried out for amplification of: DNA (ipt126tp) encoding a polypeptide (corresponding to the region between amino acid nos. 1 (Met) and 126 (Ala) of the amino acid sequence encoded by the ipt gene) having the amino acid sequence set forth in SEQ ID NO: 30; DNA (ipt59tp) encoding a polypeptide (corresponding to the region between amino acid nos. 1 (Met) and 59 (Leu) of the amino acid sequence encoded by the ipt gene) having the amino acid sequence set forth in SEQ ID NO: 32; and DNA (ipt89tp) encoding a polypeptide (corresponding to the region between amino acid nos. 1 (Met) and 89 (Ala) of the amino acid sequence encoded by the ipt gene) having the amino acid sequence set forth in SEQ ID NO: 34. The following combinations of primers were used: a primer A1 (SEQ ID NO: 25) and a primer A2 (SEQ ID NO: 26) for PCR of DNA (ipt126tp); a primer A1 (SEQ ID NO: 25) and a primer A3 (SEQ ID NO: 27) for PCR of DNA (ipt59tp); and a primer A1 (SEQ ID NO: 25) and a primer A4 (SEQ ID NO: 28) for PCR of DNA (ipt89tp). Each DNA was first cloned into a vector with the use of a TOPOTA cloning kit (Invitrogen). Then, the nucleotide sequence thereof was confirmed using ABI310. The nucleotide sequences of the ipt126tp, ipt59tp, and ipt89tp genes were set forth in SEQ ID NOS: 29, 31, and 33, respectively.

With the use of pKT123 of Example 3 as a basic vector, pKT183 (containing ipt126tp), pKT192 (containing ipt59tp), and pKT193 (containing ipt89tp) were constructed by replacing pet/tp with ipt126tp, ipt59tp, and ipt89tp, respectively (FIG. 6). Three types of petunia plants into which vectors (pKT183, pKT192, pKT193) each comprising a different above gene had been introduced were obtained (24, 34 (2 individuals of which have been blossoming until the completion of the experiment), and 36 individuals, respectively) by the method of Example 6.

Example 12

Detection of Chromoplast Transit Peptide Activity in a Capsanthin-Capsorubin Synthase Gene and that in the *Agrobacterium* Cytokinin Synthase Gene Individuals obtained via transformation with different vectors (pKT182, pKT183, and pKT192) and 10 individuals of a petunia nontransformant (*Petunia hybrida*: light yellowish petunia (a breeding line of Kirin Beer Kabushiki Kaisha)) were each placed in a pot (diameter: 9 cm) accommodating culture soil (composition: Akadama (small): leaf mold: vermiculite=6:3:1), followed by cultivation according to a conventional method. Then, flowering was induced in a biohazard greenhouse. The flower color of each transformed petunia was evaluated by comparing the flower color upon flowering with JHS color chart (the Japan color standard for horticultural plants (edited by the Ministry of Agriculture, Forestry and Fisheries of Japan, published by the Japan Color Research Institute)) and by carrying out chromaticity measurement of the flower color upon flowering based on the L*a*b* color system (Japanese Industrial Standards: JIS Z 8729). Chromaticity measurement based on the L*a*b* color system (Japanese Industrial Standards: JIS Z 8729) was carried out as follows. 3 petals of each individual from each line (provided that petals of all the individuals of the transformed petunias had fully opened after flowering) were subjected to the measurement of chromaticity 3 times with the use of a handy spectrophotometer (NF333; Nippon Denshoku). Then, the average of the values was calculated. The results relative to those obtained from the nontransformant were classified into different levels on the basis of color difference ΔE (Japanese Industrial Standards: JIS Z 8730) of the L*a*b*color system. The number of bloomed flowers at each level was obtained. The levels are expressed as follows:

−: no change in color tone (ΔE<5);

+: light orange color (5≦ΔE<20);

++: orange color (20≦ΔE<35); and

+++: deep orange color (35≦ΔE).

Table 5 shows occurrence rates of individuals having orange flower colors derived from plants transformed with different vectors.

TABLE 5

| Vector | tp | Transgene | Number of bloomed individuals | Orange-colored individuals relative to bloomed individuals | Orange-colored individuals relative to bloomed individuals (at each level) | | | | | | |
|---|---|---|---|---|---|---|---|---|---|---|---|
| | | | | | +++ | (%) | ++ | (%) | + | (%) | − | (%) |
| pKT182 | ccs/tp | ScrtW | 37 | 4 | 11% | 0 | 0% | 0 | 0% | 4 | 11% | 33 | 89% |
| pKT183 | ipt126tp | ScrtW | 24 | 10 | 42% | 3 | 13% | 4 | 17% | 3 | 13% | 14 | 58% |
| pKT192 | ipt59tp | ScrtW | 2 | 2 | 100% | 0 | 0% | 1 | 50% | 1 | 50% | 0 | 0% |

Surprisingly, those transformed with pKT183 (transit peptide: ipt126tp; transgene:ScrtW) had deeper colors than those transformed with pKT123. In addition, in terms of color tone, the number of those transformed with pKT183 with a lightly reddish color was greater than that of those transformed with pKT123. The results suggest that ipt gene products have very high capacities for transporting to chromoplasts. It is thought that the results in the case of pKT192 reflect the fact that the number of individuals examined was small. However, the capacity of transporting to chromoplasts was clearly observed also in such case. Hitherto, a moderate level of such capacity had been observed. Table 6 shows results of comparison in terms of petal color. For such comparison, the color expressed in a single petal of each individual (2 individuals (line nos.: 8 and 21) selected from among 3 individuals transformed with pKT183, each individual being evaluated at the level "+++") was directly measured using a handy spectrophotometer (NF333). Then, the results were compared with those obtained from a nontransformant (1 individual). Measurement was carried out 3 times. Thereafter, the average of the obtained numerical values was calculated. The increase in numerical values of a* indicates an increased influence of a red factor upon color tone. In addition, such color measurement is an alternative means for describing observed color phenotypes. Thus, such codes should be regarded as indices of observed colors. Therefore, potential colors that can be obtained in accordance with the present invention are not limited thereto.

Figure 7:
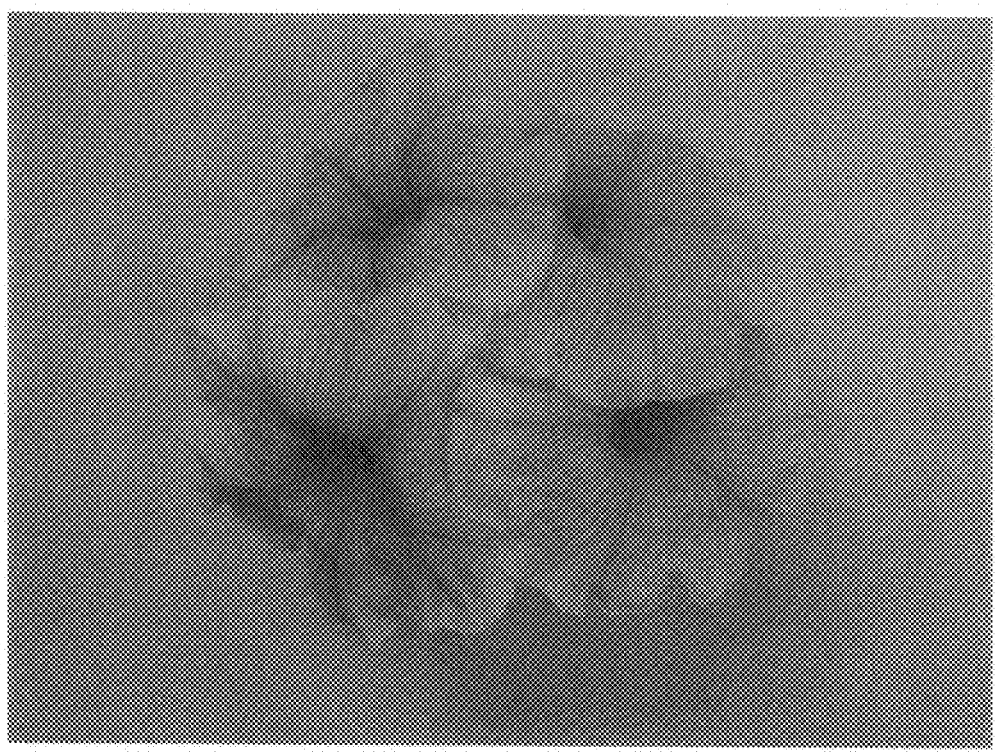
FIG. 7 shows an image for comparison of petals of a transformant transformed with pKT183, those of a transformant transformed with pKT123, and those of a nontransformant (pKT183 (line nos.: 8 and 21), pKT123 (line no.: 3), and a nontransformant, counterclockwise from the upper left).

In addition, FIG. 7 shows an image for comparison of petals obtained from transformants transformed with pKT183 (line nos.: 8 and 21), a transformant transformed with pKT123 (line no.: 3), and a nontransformant.

TABLE 6

| Line no. | L* | a* | b* | ΔE |
|---|---|---|---|---|
| Nontransformant | 71.05 | −11.27 | 81.49 | |
| 8 | 54.74 | 31.54 | 49.47 | 55.89 |
| 21 | 53.40 | 29.87 | 52.40 | 53.38 |

INDUSTRIAL APPLICABILITY

The range of yellowish flower colors of ornamental flowers can be expanded with the use of the transit peptide and the method of producing a plant with the use of the same of the present invention. Thus, the peptide and the method of the present invention are useful for development of ornamental plants.

The invention claimed is:

1. A recombinant vector containing a fused gene formed of:

(A) a gene according to (i) (ii), (iii), (iv), or (v):
  (i) a gene encoding a peptide consisting of the amino acid sequence set forth in SEQ ID NO: 30, 32, or 34;
  (ii) a gene encoding a peptide consisting of an amino acid sequence derived from the amino acid sequence set forth in SEQ ID NO: 30, 32, or 34 by deletion, substitution, insertion, or addition of one or several amino acids and having transport activity to chromoplasts in petals;
  (iii) a gene consisting of DNA consisting of the nucleotide sequence set forth in SEQ ID NO: 29, 31, or 33;
  (iv) a gene consisting of DNA that hybridizes under stringent conditions to DNA consisting of a nucleotide sequence complementary to DNA consisting of the nucleotide sequence set forth in SEQ ID NO: 29, 31, or 33 and that encodes a peptide having transport activity to chromoplasts in petals; or
  (v) a gene consisting of DNA that consists of a nucleotide sequence at least 80% homologous to the nucleotide sequence set forth in SEQ ID NO: 29, 31, or 33 and that encodes a peptide having transport activity to chromoplasts in petals; and (B) one, or two or more genes encoding an enzyme protein involved in the carotenoid biosynthetic pathway.

2. The recombinant vector according to claim 1, wherein the enzyme protein involved in the carotenoid biosynthetic pathway is a 1-deoxy-D-xylose-5-phosphate synthase, an isopentenyl diphosphate isomerase, a geranylgeranyl pyrophosphate synthase, a phytoene synthase, a lycopene synthase, a β-cyclase, ketolase, or a capsanthin-capsorubin synthase.

3. A plant cell into which the recombinant vector according to claim 1 has been introduced.

4. A plant cell into which a fused gene consisting of the nucleotide sequence set forth in SEQ ID NO: 29 and a gene consisting of the nucleotide sequence set forth in SEQ ID NO: 5 has been introduced.

5. A method of producing a plant having yellowish petals, comprising
(A) introducing into a plant cell a fused gene formed of
  (a) a gene according to (i) (ii), (iii), (iv), or (v):
    (i) a gene encoding a peptide consisting of the amino acid sequence set forth in SEQ ID NO: 30, 32, or 34;
    (ii) a gene encoding a peptide consisting of an amino acid sequence derived from the amino acid sequence set forth in SEQ ID NO: 30, 32, or 34 by deletion, substitution, insertion, or addition of one or several amino acids and having transport activity to chromoplasts in petals;
    (iii) a gene consisting of DNA consisting of the nucleotide sequence set forth in SEQ ID NO: 29, 31, or 33;
    (iv) a gene consisting of DNA that hybridizes under stringent conditions to DNA consisting of a nucleotide sequence complementary to DNA consisting of the nucleotide sequence set forth in SEQ ID NO: 29, 31, or 33 and that encodes a peptide having transport activity to chromoplasts in petals; or
    (v) a gene consisting of DNA that consists of a nucleotide sequence at least 80% homologous to the nucleotide sequence set forth in SEQ ID NO: 29, 31, or 33 and that encodes a peptide having transport activity to chromoplasts in petals; and
  (b) one, or two or more genes encoding an enzyme protein involved in the carotenoid biosynthetic pathway; and
(B) regenerating a plant from the plant cell.

6. A plant cell into which the recombinant vector according to claim 2 has been introduced.

7. The method according to claim 5, wherein the enzyme protein involved in the carotenoid biosynthetic pathway is a 1-deoxy-D-xylose-5-phosphate synthase, an isopentenyl diphosphate isomerase, a geranylgeranyl pyrophosphate synthase, a phytoene synthase, a lycopene synthase, a β-cyclase, ketolase, or a capsanthin-capsorubin synthase.

* * * * *

SEQUENCE LISTING

```
<160> NUMBER OF SEQ ID NOS: 35

<210> SEQ ID NO 1
<211> LENGTH: 177
<212> TYPE: DNA
<213> ORGANISM: Petunia hybrida
<220> FEATURE:
<221> NAME/KEY: CDS
<222> LOCATION: (1)..(177)

<400> SEQUENCE: 1 atg gct tcc atc tct tct cta aat caa ttt cca tgc aaa act cta caa      48
Met Ala Ser Ile Ser Ser Leu Asn Gln Phe Pro Cys Lys Thr Leu Gln
 1               5                  10                  15 ctc aca tct caa ttc tca aaa cca acc tca aat atc tca tcc ttt cca      96
Leu Thr Ser Gln Phe Ser Lys Pro Thr Ser Asn Ile Ser Ser Phe Pro
             20                  25                  30 ata ttc tca tca aaa aca gaa caa caa aag cca att tca ctt caa gaa     144
Ile Phe Ser Ser Lys Thr Glu Gln Gln Lys Pro Ile Ser Leu Gln Glu
         35                  40                  45 tac aca aac aca aga tca aga gtc aca gta aaa                         177
Tyr Thr Asn Thr Arg Ser Arg Val Thr Val Lys
     50                  55

<210> SEQ ID NO 2
<211> LENGTH: 59
<212> TYPE: PRT
<213> ORGANISM: Petunia hybrida

<400> SEQUENCE: 2

Met Ala Ser Ile Ser Ser Leu Asn Gln Phe Pro Cys Lys Thr Leu Gln
 1               5                  10                  15

Leu Thr Ser Gln Phe Ser Lys Pro Thr Ser Asn Ile Ser Ser Phe Pro
             20                  25                  30

Ile Phe Ser Ser Lys Thr Glu Gln Gln Lys Pro Ile Ser Leu Gln Glu
         35                  40                  45

Tyr Thr Asn Thr Arg Ser Arg Val Thr Val Lys
     50                  55

<210> SEQ ID NO 3
<211> LENGTH: 117
<212> TYPE: DNA
<213> ORGANISM: Capsicum annuum
<220> FEATURE:
<221> NAME/KEY: CDS
```

<222> LOCATION: (1)..(117)

<400> SEQUENCE: 3

```
atg gaa acc ctt cta aag cct ttt cca tct cct tta ctt tcc att cct        48
Met Glu Thr Leu Leu Lys Pro Phe Pro Ser Pro Leu Leu Ser Ile Pro
 1               5                  10                  15 act cct aac atg tat agt ttc aaa cac aac tcc act ttt cca aat cca        96
Thr Pro Asn Met Tyr Ser Phe Lys His Asn Ser Thr Phe Pro Asn Pro
             20                  25                  30 acc aaa caa aaa gat tca aga                                           117
Thr Lys Gln Lys Asp Ser Arg
         35
```

<210> SEQ ID NO 4
<211> LENGTH: 39
<212> TYPE: PRT
<213> ORGANISM: Capsicum annuum

<400> SEQUENCE: 4

```
Met Glu Thr Leu Leu Lys Pro Phe Pro Ser Pro Leu Leu Ser Ile Pro
 1               5                  10                  15

Thr Pro Asn Met Tyr Ser Phe Lys His Asn Ser Thr Phe Pro Asn Pro
             20                  25                  30

Thr Lys Gln Lys Asp Ser Arg
         35
```

<210> SEQ ID NO 5
<211> LENGTH: 729
<212> TYPE: DNA
<213> ORGANISM: Agrobacterium aurantiacum

<400> SEQUENCE: 5

| | |
|---|---|
| atgtccgctc acgctttgcc aaaggctgac ttgactgcta cctccttgat cgtctccggt | 60 |
| ggtatcatcg ctgcttggtt ggcttttgcac gttcacgctt tgtggttctt ggacgctgct | 120 |
| gctcacccaa tcttggctat cgctaacttc ttgggtttga cctggttgtc tgtcggtttg | 180 |
| ttcatcatcg ctcacgacgc tatgcacggt tccgttgtcc caggtagacc aagagctaac | 240 |
| gctgctatgg gtcaattggt tttgtggttg tacgctggtt tctcttggag aaagatgatc | 300 |
| gttaagcaca tggctcacca cagacacgct ggtactgatg acgacccaga tttcgaccac | 360 |
| ggtggtccag ttagatggta cgctagattc atcggtactt acttcggttg agagagggt | 420 |
| ttgttgttgc cagtcatcgt taccgtttac gctttgatct tgggtgacag atggatgtac | 480 |
| gttgtcttct ggccattgcc atccatcttg gcttctatcc aattgttcgt tttcggtacc | 540 |
| tggttgccac acagaccagg tcacgacgct ttcccagaca gacacaacgc tagatcctcc | 600 |
| agaatctctg atccagtttc cttgttgacc tgtttccact tcggtggtta ccaccacgag | 660 |
| caccacttgc acccaactgt cccatggtgg agattgccat ccaccagaac caagggtgac | 720 |
| accgcttag | 729 |

<210> SEQ ID NO 6
<211> LENGTH: 729
<212> TYPE: DNA
<213> ORGANISM: Alcaligenes sp.

<400> SEQUENCE: 6

| | |
|---|---|
| atgtccggac ggaagcctgg cacaactggc gacacgatcg tcaatctcgg tctgaccgcc | 60 |
| gcgatcctgc tgtgctggct ggtcctgcac gtctttacgc tatggttgct agatgcggcc | 120 |
| gcgcatccgc tgcttgccgt gctgtgcctg gctgggctga cctggctgtc ggtcgggctg | 180 |

```
ttcatcatcg cgcatgacgc aatgcacggg tccgtggtgc cggggcggcc gcgcgccaat    240
gcggcgatcg ggcaactggc gctgtggctc tatgcggggt tctcgtggcc caagctgatc    300
gccaagcaca tggcgcatca ccggcacgcc ggcaccgacg acgatcccga tttcggtcac    360
ggagggcccg tgcgctggta cggcagcttc gtctccacct atttcggctg gcgagaggga    420
ctgctgctac cggtgatcgt caccacctat gcgctgatcc tgggcgatcg ctggatgtat    480
gtcatcttct ggccggtccc ggccgttctg gcgtcgatcc agcttttcgt cttcggaact    540
tggctgcccc accgcccggg acatgacgat tttcccgacc ggcacaacgc gaggtcgacc    600
ggcatcggcg accgttgtc actactgacc tgcttccatt tcggcggcta tcaccacgaa     660
catcacctgc atccgcatgt gccgtggtgg cgcctgcctc gtacacgcaa gaccggaggc    720
cgcgcatga                                                            729

<210> SEQ ID NO 7
<211> LENGTH: 963
<212> TYPE: DNA
<213> ORGANISM: Haematococcus pluvialis

<400> SEQUENCE: 7
atgcacgtcg catcggcact aatggtcgag cagaaaggca gtgaggcagc tgcttccagc     60
ccagacgtct tgagagcgtg ggcgacacag tatcacatgc catccgagtc gtcagacgca    120
gctcgtcctg cgctaaagca cgcctacaaa cctccagcat ctgacgccaa gggcatcacg    180
atggcgctga ccatcattgg cacctggacc gcagtgtttt tacacgcaat atttcaaatc    240
aggctaccga catccatgga ccagcttcac tggttgcctg tgtccgaagc cacagcccag    300
cttttgggcg gaagcagcag cctactgcac atcgctgcag tcttcattgt acttgagttc    360
ctgtacactg gtctattcat caccacacat gacgcaatgc atggcaccat agctttgagg    420
cacaggcagc tcaatgatct ccttggcaac atctgcatat cactgtacgc ctggtttgac    480
tacagcatgc tgcatcgcaa gcactgggag caccacaacc atactggcga agtggggaaa    540
gaccctgact ccacaagggg aaatcccggc cttgtcccct ggttcgccag cttcatgtcc    600
agctacatgt ccctgtggca gttttgcccgg ctggcatggt gggcagtggt gatgcaaatg    660 ctggggggcgc ccatggcaaa tctcctagtc ttcatggctg cagccccaat cttgtcagca    720
ttccgcctct tctacttcgg cacttacctg ccacacaagc ctgagccagg ccctgcagca    780
ggctctcagg tgatggcctg gttcagggcc aagacaagtg aggcatctga tgtgatgagt    840
ttcctgacat gctaccactt tgacctgcac tgggagcacc acaggtggcc cttttgccccc    900 tggtggcagc tgccccactg ccgccgcctg tccgggcgtg gcctggtgcc tgccttggca    960
tga                                                                  963

<210> SEQ ID NO 8
<211> LENGTH: 909
<212> TYPE: DNA
<213> ORGANISM: Ervinia uredovora

<400> SEQUENCE: 8
atgacggtct gcgcaaaaaa acacgttcat ctcactcgcg atgctgcgga gcagttactg     60
gctgatattg atcgacgcct tgatcagtta ttgcccgtgg agggagaacg ggatgttgtg    120
ggtgccgcga tgcgtgaagg tgcgctggca ccgggaaaac gtattcgccc catgttgctg    180
ttgctgaccg cccgcgatct gggttgcgct gtcagccatg acggattact ggatttggcc    240
tgtgcggtgg aaatggtcca cgcggcttcg ctgatccttg acgatatgcc ctgcatggac    300
```

| | |
|---|---|
| gatgcgaagc tgcggcgcgg acgccctacc attcattctc attacggaga gcatgtggca | 360 |
| atactggcgg cggttgcctt gctgagtaaa gcctttggcg taattgccga tgcagatggc | 420 |
| ctcacgccgc tggcaaaaaa tcgggcggtt tctgaactgt caaacgccat cggcatgcaa | 480 |
| ggattggttc agggtcagtt caaggatctg tctgaagggg ataagccgcg cagcgctgaa | 540 |
| gctattttga tgacgaatca ctttaaaacc agcacgctgt tttgtgcctc catgcagatg | 600 |
| gcctcgattg ttgcgaatgc ctccagcgaa gcgcgtgatt gcctgcatcg ttttcactt | 660 |
| gatcttggtc aggcatttca actgctgac gatttgaccg atggcatgac cgacaccggt | 720 |
| aaggatagca atcaggacgc cggtaaatcg acgctggtca atctgttagg cccgagggcg | 780 |
| gttgaagaac gtctgagaca acatcttcag cttgccagtg agcatctctc tgcggcctgc | 840 |
| caacacgggc acgccactca acattttatt caggcctggt tgacaaaaa actcgctgcc | 900 |
| gtcagttaa | 909 |

<210> SEQ ID NO 9
<211> LENGTH: 930
<212> TYPE: DNA
<213> ORGANISM: Ervinia uredovora

<400> SEQUENCE: 9

| | |
|---|---|
| atgaataatc cgtcgttact caatcatgcg gtcgaaacga tggcagttgg ctcgaaaagt | 60 |
| tttgcgacag cctcaaagtt atttgatgca aaaacccggc gcagcgtact gatgctctac | 120 |
| gcctggtgcc gccattgtga cgatgttatt gacgatcaga cgctgggctt tcaggcccgg | 180 |
| cagcctgcct tacaaacgcc cgaacaacgt ctgatgcaac ttgagatgaa aacgcgccag | 240 |
| gcctatgcag gatcgcagat gcacgaaccg gcgtttgcgg cttttcagga gtggcctatg | 300 |
| gctcatgata tcgccccggc ttacgcgttt gatcatctgg aaggcttcgc catggatgta | 360 |
| cgcgaagcgc aatacagcca actgatgat acgctgcgct attgctatca cgttgcaggc | 420 |
| gttgtcggct tgatgatggc gcaaatcatg ggcgtgcggg ataacgccac gctggaccgc | 480 |
| gcctgtgacc ttgggctggc atttcagttg accaatattg ctcgcgatat tgtgacgat | 540 |
| gcgcatgcgg gccgctgtta tctgccggca agctggctgg agcatgaagg tctgaacaaa | 600 |
| gagaattatg cggcacctga aaccgtcag gcgctgagcc gtatcgcccg tcgtttggtg | 660 |
| caggaagcag aaccttacta tttgtctgcc acagccggcc tggcagggt gccctgcgt | 720 |
| tccgcctggg caatcgctac ggcgaagcag gtttaccgga aataggtgt caaagttgaa | 780 |
| caggccggtc agcaagcctg ggatcagcgg cagtcaacga ccacgcccga aaaattaacg | 840 |
| ctgctgctgg ccgcctctgg tcaggcccctt acttcccgga tgcgggctca tcctccccgc | 900 |
| cctgcgcatc tctggcagcg cccgctctag | 930 |

<210> SEQ ID NO 10
<211> LENGTH: 1479
<212> TYPE: DNA
<213> ORGANISM: Ervinia uredovora

<400> SEQUENCE: 10

| | |
|---|---|
| atgaaaccaa ctacggtaat tggtgcaggc ttcggtggcc tggcactggc aattcgtcta | 60 |
| caagctgcgg ggatcccgt cttactgctt gaacaacgta taaacccgg cggtcgggct | 120 |
| tatgtctacg aggatcaggg gtttaccttt gatgcaggcc cgacggttat caccgatccc | 180 |
| agtgccattg aagaactgtt tgcactggca ggaaaacagt aaaagagta tgtcgaactg | 240 |
| ctgccggtta cgccgtttta ccgcctgtgt tgggagtcag ggaaggtctt taattacgat | 300 |

```
aacgatcaaa cccggctcga agcgcagatt cagcagttta atccccgcga tgtcgaaggt    360
tatcgtcagt ttctggacta ttcacgcgcg gtgtttaaag aaggctatct aaagctcggt    420
actgtccctt ttttatcgtt cagagacatg cttcgcgccg cacctcaact ggcgaaactg    480
caggcatgga gaagcgttta cagtaaggtt gccagttaca tcgaagatga acatctgcgc    540
caggcgtttt ctttccactc gctgttggtg ggcggcaatc ccttcgccac ctcatccatt    600
tatacgttga tacacgcgct ggagcgtgag tgggcgtct  ggtttccgcg tggcggcacc    660
ggcgcattag ttcaggggat gataaagctg tttcaggatc tgggtggcga agtcgtgtta    720
aacgccagag tcagccatat ggaaacgaca ggaaacaaga ttgaagccgt gcatttagag    780
gacggtcgca ggttcctgac gcaagccgtc gcgtcaaatg cagatgtggt tcatacctat    840
cgcgacctgt taagccagca ccctgccgcg gttaagcagt ccaacaaact gcagactaag    900
cgcatgagta actctctgtt tgtgctctat tttggtttga atcaccatca tgatcagctc    960
gcgcatcaca cggtttgttt cggcccgcgt taccgcgagc tgattgacga aattttttaat   1020 catgatggcc tcgcagagga cttctcactt tatctgcacg cgccctgtgt cacggattcg   1080
tcactggcgc ctgaaggttg cggcagttac tatgtgttgg cgccggtgcc gcatttaggc   1140
accgcgaacc tcgactggac ggttgagggg ccaaaactac gcgaccgtat ttttgcgtac   1200
cttgagcagc attacatgcc tggcttacgg agtcagctgg tcacgcaccg gatgtttacg   1260
ccgtttgatt ttcgcgacca gcttaatgcc tatcatggct cagccttttc tgtggagccc   1320
gttcttaccc agagcgcctg gtttcggcc cataaccgcg ataaaccat tactaatctc    1380 tacctggtcg gcgcaggcac gcatcccggc gcaggcattc ctggcgtcat cggctcggca   1440
aaagcgacag caggtttgat gctggaggat ctgatatga                          1479

<210> SEQ ID NO 11
<211> LENGTH: 1149
<212> TYPE: DNA
<213> ORGANISM: Ervinia uredovora

<400> SEQUENCE: 11
atgcaaccgc attatgatct gattctcgtg ggggctggac tcgcgaatgg ccttatcgcc     60
ctgcgtcttc agcagcagca acctgatatg cgtattttgc ttatcgacgc cgcacccag    120 gcgggcggga atcatacgtg gtcatttcac cacgatgatt tgactgagag ccaacatcgt    180
tggatagctc cgctggtggt tcatcactgg cccgactatc aggtacgctt cccacacgc    240 cgtcgtaagc tgaacagcgg ctacttttgt attacttctc agcgtttcgc tgaggtttta    300
cagcgacagt ttggcccgca cttgtggatg gataccgcgg tcgcagaggt taatgcggaa    360
tctgttcggt tgaaaaaggg tcaggttatc ggtgcccgcg cggtgattga cgggcggggt    420
tatgcggcaa attcagcact gagcgtgggc ttccaggcgt ttattggcca ggaatggcga    480
ttgagccacc cgcatggttt atcgtctccc attatcatgg atgccacggt cgatcagcaa    540
aatggttatc gcttcgtgta cagcctgccg ctctcgccga ccagattgtt aattgaagac    600
acgcactata ttgataatgc gacattagat cctgaatgcg cgcggcaaaa tatttgcgac    660
tatgccgcgc aacagggttg gcagcttcag acactgctgc gagaagaaca gggcgcctta    720
cccattactc tgtcgggcaa tgccgacgca ttctggcagc agcgccccct ggcctgtagt    780
ggattacgtg ccggtctgtt ccatcctacc accggctatt cactgccgct ggcggttgcc    840
gtggccgacc gctgagtgc acttgatgtc tttacgtcgg cctcaattca ccatgccatt    900
acgcattttg cccgcgagcg ctggcagcag caggctttt tccgcatgct gaatcgcatg    960
```

```
ctgttttag ccggacccgc cgattcacgc tggcgggtta tgcagcgttt ttatggttta    1020
cctgaagatt taattgcccg ttttttatgcg ggaaaactca cgctgaccga tcggctacgt    1080
attctgagcg gcaagccgcc tgttccggta ttagcagcat tgcaagccat tatgacgact    1140
catcgttaa                                                             1149

<210> SEQ ID NO 12
<211> LENGTH: 867
<212> TYPE: DNA
<213> ORGANISM: Saccharomyces cerevisiae

<400> SEQUENCE: 12
atgactgccg acaacaatag tatgccccat ggtgcagtat ctagttacgc caaattagtg     60
caaaaccaaa cacctgaaga cattttggaa gagtttcctg aaattattcc attacaacaa    120
agacctaata cccgatctag tgagacgtca aatgacgaaa gcggagaaac atgttttttct    180 ggtcatgatg aggagcaaat taagttaatg aatgaaaatt gtattgtttt ggattgggac    240
gataatgcta ttggtgccgg taccaagaaa gtttgtcatt taatgaaaaa tattgaaaag    300
ggtttactac atcgtgcatt ctccgtcttt attttcaatg aacaaggtga attacttta    360 caacaaagag ccactgaaaa aataactttc cctgatcttt ggactaacac atgctgctct    420
catccactat gtattgatga cgaattaggt ttgaagggta agctagacga taagattaag    480
ggcgctatta ctgcggcggt gagaaaacta gatcatgaat taggtattcc agaagatgaa    540
actaagacaa ggggtaagtt tcactttta aacagaatcc attacatggc accaagcaat    600
gaaccatggg gtgaacatga aattgattac atcctatttt ataagatcaa cgctaaagaa    660
aacttgactg tcaacccaaa cgtcaatgaa gttagagact tcaaatgggt ttcaccaaat    720
gatttgaaaa ctatgtttgc tgacccaagt tacaagttta cgccttggtt taagattatt    780
tgcgagaatt acttattcaa ctggtgggag caattagatg accttttctga agtggaaaat    840 gacaggcaaa ttcatagaat gctataa                                        867

<210> SEQ ID NO 13
<211> LENGTH: 1863
<212> TYPE: DNA
<213> ORGANISM: Escherichia coli

<400> SEQUENCE: 13
atgagttttg atattgccaa ataccccgacc ctggcactgg tcgactccac ccaggagtta     60
cgactgttgc cgaaagagag tttaccgaaa ctctgcgacg aactgcgccg ctatttactc    120
gacagcgtga gccgttccag cgggcacttc gcctccgggc tggcacggt cgaactgacc    180 gtggcgctgc actatgtcta caacaccccg tttgaccaat tgatttggga tgtggggcat    240
caggcttatc cgcataaaat tttgaccgga cgccgcgaca aaatcggcac catccgtcag    300
aaaggcggtc tgcacccgtt cccgtggcgc ggcgaaagcg aatatgacgt attaagcgtc    360
gggcattcat caacctccat cagtgccgga attggtattg cggttgctgc gaaaaagaa    420 ggcaaaaatc gccgcaccgt ctgtgtcatt ggcgatggcg cgattaccgc aggcatggcg    480
tttgaagcga tgaatcacgc gggcgatatc cgtcctgata tgctggtgat tctcaacgac    540
aatgaaatgt cgatttccga aaatgtcggc gcgctcaaca accatctggc acagctgctt    600
tccggtaagc tttactcttc actgcgcgaa ggcgggaaaa agttttctc tggcgtgccg    660 ccaattaaag agctgctcaa acgcaccgaa gaacatatta aaggcatggt agtgcctggc    720
acgttgtttg aagagctggg cttaactac atcggcccgg tggacggtca cgatgtgctg    780
```

```
gggcttatca ccacgctaaa gaacatgcgc gacctgaaag gcccgcagtt cctgcatatc      840
atgaccaaaa aaggtcgtgg ttatgaaccg gcagaaaaag acccgatcac tttccacgcc      900
gtgcctaaat tgatccctc cagcggttgt ttgccgaaaa gtagcggcgg tttgccgagc       960
tattcaaaaa tctttggcga ctggttgtgc gaaacggcag cgaaagacaa caagctgatg     1020
gcgattactc cggcgatgcg tgaaggttcc ggcatggtcg agttttcacg taaattcccg     1080
gatcgctact tcgacgtggc aattgccgag caacacgcgg tgacctttgc tgcgggtctg     1140
gcgattggtg ggtacaaacc cattgtcgcg atttactcca ctttcctgca acgcgcctat     1200
gatcaggtgc tgcatgacgt ggcgattcaa aagcttccgg tcctgttcgc catcgaccgc     1260 gcggcattg ttggtgctga cggtcaaacc catcagggtg cttttgatct ctcttacctg      1320
cgctgcatac cggaaatggt cattatgacc ccgagcgatg aaaacgaatg tcgccagatg     1380
ctctataccg gctatcacta taacgatggc ccgtcagcgg tgcgctaccc gcgtggcaac     1440
gcggtcggcg tggaactgac gccgctgaaa aaactaccaa ttggcaaagg cattgtgaag     1500
cgtcgtggcg agaaactggc gatccttaac tttggtacgc tgatgccaga agcggcgaaa     1560
gtcgccgaat cgctgaacgc cacgctggtc gatatgcgtt ttgtgaaacc gcttgatgaa     1620
gcgttaattc tggaaatggc cgccagccat gaagcgctgg tcaccgtaga agaaaacgcc     1680
attatgggcg gcgcaggcag cggcgtgaac gaagtgctga tggcccatcg taaaccagta     1740
cccgtgctga acattggcct gccggacttc tttattccgc aaggaactca ggaagaaatg     1800
cgcgccgaac tcggcctcga tgccgctggt atggaagcca aaatcaaggc ctggctggca     1860
taa                                                                   1863

<210> SEQ ID NO 14
<211> LENGTH: 1497
<212> TYPE: DNA
<213> ORGANISM: Capsicum annuum

<400> SEQUENCE: 14
atggaaaccc ttctaaagcc ttttccatct cctttacttt ccattcctac tcctaacatg       60
tatagtttca aacacaactc cacttttcca aatccaacca acaaaaaga ttcaagaaag       120 ttccattata gaaacaaaag cagtacacat ttttgtagct ttcttgattt agcacccaca      180
tcaaagccag agtctttaga tgttaacatc tcatgggttg atactgatct ggacggggct      240
gaattcgacg tgatcatcat tggaactggc cctgccgggc ttcggctagc tgaacaagtt      300
tctaaatatg gtattaaggt atgttgcgtt gacccttcac cactttccat gtggccaaat      360
aattatggtg tttgggttga tgagtttgaa aagttgggat tagaagattg tctagatcat      420
aagtggcctg tgagttgtgt tcatataagt gatcacaaga ctaagtattt ggacagacca      480
tatggtagag taagtagaaa gaagttgaag ttgaaattgt tgaatagttg tgttgaaaat      540
agagtgaagt tttataaagc caaggttttg aaagtgaagc atgaagaatt tgagtcttcg      600
attgtttgtg atgatggtag gaagataagc ggtagcttga ttgttgatgc aagtggctat      660
gctagtgatt ttatagagta tgacaagcca agaaaccatg ttatcaagt tgctcatggg      720 attttagcag aagttgataa tcatccattt gatttggata aaatgatgct tatggattgg      780
agggattctc atttaggtaa tgagccatat ctgagggtga agaatactaa agaaccaaca      840 ttccttgtatg caatgccatt tgataggaat ttggtattct tggaagagac ttctttagtg      900
agtcggccta tgttatcgta tatggaagtg aaaagaagga tggtagcaag attaagacat      960
ttggggatca aagtgagaag tgtccttgag gaagagaagt gtgtgatcac tatgggagga      1020
```

```
ccacttccgc ggattcctca aaatgttatg gctattggtg ggacttcagg gatagttcat   1080
ccatcgtctg gtacatggt ggctcgtagc atggcattgg caccagtact ggctgaggcc     1140
atcgtcgaaa gccttggctc aacaagaatt ataagagggt ctcaactttta ccatagagtt   1200 tggaatggtt tgtggccttc ggatagaaga cgtgttagag aatgttattg tttcggaatg   1260
gagactttgt tgaagcttga tttggaaggt actaggagat tgtttgatgc tttctttgat   1320
gttgatccca agtactggca cgggttcctt tcttcaagat tgtctgtcaa agaacttgct   1380
gtactcagtt tgtacctttt tggacatgcc tctaatttgg ctaggttgga tattgttaca   1440
aagtgcactg tccccttggt taaactgctg ggcaatctag caatagagag cctttga       1497
```

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
cagctggaat ccaagaaccc ta                                               22
```

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
gtaagtggtc agcagccatg at                                               22
```

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
actagtacgg cttttactgt gactcttg                                         28
```

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
tctagattct tcactcattt cctctc                                           26
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
agatctttca aaggctctct attgctagat                                    30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
actagttttt tttcactata ctatatcacc                                    30

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
taaagcacga ggaagcggt                                                19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcacaacaga caatcggct                                                19

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
catatggaaa cccttctaaa gcc                                           23

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
actagtaact ttcttgaatc tttttg                                        26

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
catatggatc tacgtctaat ttt                                           23
```

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actagtgcta actcgttgcg aataa                                          25

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
actagtagac gagtcgttcc tttcag                                         26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
actagtttgg cctcgtgatt gtgcac                                         26

<210> SEQ ID NO 29
<211> LENGTH: 378
<212> TYPE: DNA
<213> ORGANISM: Agrobacterium tumefaciens
<220> FEATURE:
<221> NAME/KEY: CDS
<222> LOCATION: (1)..(378)

<400> SEQUENCE: 29

```
atg gat cta cgt cta att ttc ggt cca act tgc aca gga aag aca tcg      48
Met Asp Leu Arg Leu Ile Phe Gly Pro Thr Cys Thr Gly Lys Thr Ser
 1               5                  10                  15 act gcg ata gct ctt gcc cag cag act ggc ctc cca gtc ctc tcg ctc      96
Thr Ala Ile Ala Leu Ala Gln Gln Thr Gly Leu Pro Val Leu Ser Leu
             20                  25                  30 gat cgc gtc caa tgc tgt cct caa cta tca acc gga agc ggg cga cca     144
Asp Arg Val Gln Cys Cys Pro Gln Leu Ser Thr Gly Ser Gly Arg Pro
         35                  40                  45 aca gtg gaa gaa ctg aaa gga acg act cgt ctg tac ctt gat gat cgc     192
Thr Val Glu Glu Leu Lys Gly Thr Thr Arg Leu Tyr Leu Asp Asp Arg
     50                  55                  60 cct ttg gta aag ggt atc att aca gcc aag caa gct cat gaa cgg ctc     240
Pro Leu Val Lys Gly Ile Ile Thr Ala Lys Gln Ala His Glu Arg Leu
 65                  70                  75                  80 att gcg gag gtg cac aat cac gag gcc aaa ggc ggg ctt att ctt gag     288
Ile Ala Glu Val His Asn His Glu Ala Lys Gly Gly Leu Ile Leu Glu
                 85                  90                  95 gga gga tct atc tcg ttg ctc agg tgc atg gcg caa agt cgt tat tgg     336
Gly Gly Ser Ile Ser Leu Leu Arg Cys Met Ala Gln Ser Arg Tyr Trp
            100                 105                 110 aac gcg gat ttt cgt tgg cat att att cgc aac gag tta gca             378
Asn Ala Asp Phe Arg Trp His Ile Ile Arg Asn Glu Leu Ala
```

-continued

<210> SEQ ID NO 30
<211> LENGTH: 126
<212> TYPE: PRT
<213> ORGANISM: Agrobacterium tumefaciens

<400> SEQUENCE: 30

Met Asp Leu Arg Leu Ile Phe Gly Pro Thr Cys Thr Gly Lys Thr Ser
1               5                   10                  15

Thr Ala Ile Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Thr Arg Leu Tyr Leu Asp Asp Arg
    50                  55                  60

Pro Leu Val Lys Gly Ile Ile Thr Ala Lys Gln Ala His Glu Arg Leu
65                  70                  75                  80

Ile Ala Glu Val His Asn His Glu Ala Lys Gly Gly Leu Ile Leu Glu
                85                  90                  95

Gly Gly Ser Ile Ser Leu Leu Arg Cys Met Ala Gln Ser Arg Tyr Trp
            100                 105                 110

Asn Ala Asp Phe Arg Trp His Ile Ile Arg Asn Glu Leu Ala
        115                 120                 125

<210> SEQ ID NO 31
<211> LENGTH: 177
<212> TYPE: DNA
<213> ORGANISM: Agrobacterium tumefaciens
<220> FEATURE:
<221> NAME/KEY: CDS
<222> LOCATION: (1)..(177)

<400> SEQUENCE: 31 atg gat cta cgt cta att ttc ggt cca act tgc aca gga aag aca tcg      48
Met Asp Leu Arg Leu Ile Phe Gly Pro Thr Cys Thr Gly Lys Thr Ser
1               5                   10                  15 act gcg ata gct ctt gcc cag cag act ggc ctc cca gtc ctc tcg ctc      96
Thr Ala Ile Ala Leu Ala Gln Gln Thr Gly Leu Pro Val Leu Ser Leu
            20                  25                  30 gat cgc gtc caa tgc tgt cct caa cta tca acc gga agc ggg cga cca     144
Asp Arg Val Gln Cys Cys Pro Gln Leu Ser Thr Gly Ser Gly Arg Pro
        35                  40                  45 aca gtg gaa gaa ctg aaa gga acg act cgt ctg                         177
Thr Val Glu Glu Leu Lys Gly Thr Thr Arg Leu
    50                  55

<210> SEQ ID NO 32
<211> LENGTH: 59
<212> TYPE: PRT
<213> ORGANISM: Agrobacterium tumefaciens

<400> SEQUENCE: 32

Met Asp Leu Arg Leu Ile Phe Gly Pro Thr Cys Thr Gly Lys Thr Ser
1               5                   10                  15

Thr Ala Ile Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Thr Arg Leu
    50                  55

```
<210> SEQ ID NO 33
<211> LENGTH: 269
<212> TYPE: DNA
<213> ORGANISM: Agrobacterium tumefaciens
<220> FEATURE:
<221> NAME/KEY: CDS
<222> LOCATION: (1)..(267)

<400> SEQUENCE: 33 atg gat cta cgt cta att ttc ggt cca act tgc aca gga aag aca tcg      48
Met Asp Leu Arg Leu Ile Phe Gly Pro Thr Cys Thr Gly Lys Thr Ser
 1               5                  10                  15 act gcg ata gct ctt gcc cag cag act ggc ctc cca gtc ctc tcg ctc      96
Thr Ala Ile Ala Leu Ala Gln Gln Thr Gly Leu Pro Val Leu Ser Leu
             20                  25                  30 gat cgc gtc caa tgc tgt cct caa cta tca acc gga agc ggg cga cca     144
Asp Arg Val Gln Cys Cys Pro Gln Leu Ser Thr Gly Ser Gly Arg Pro
         35                  40                  45 aca gtg gaa gaa ctg aaa gga acg act cgt ctg tac ctt gat gat cgc     192
Thr Val Glu Glu Leu Lys Gly Thr Thr Arg Leu Tyr Leu Asp Asp Arg
     50                  55                  60 cct ttg gta aag ggt atc att aca gcc aag caa gct cat gaa cgg ctc     240
Pro Leu Val Lys Gly Ile Ile Thr Ala Lys Gln Ala His Glu Arg Leu
 65                  70                  75                  80 att gcg gag gtg cac aat cac gag gcc aa                              269
Ile Ala Glu Val His Asn His Glu Ala
                 85

<210> SEQ ID NO 34
<211> LENGTH: 89
<212> TYPE: PRT
<213> ORGANISM: Agrobacterium tumefaciens

<400> SEQUENCE: 34

Met Asp Leu Arg Leu Ile Phe Gly Pro Thr Cys Thr Gly Lys Thr Ser
 1               5                  10                  15

Thr Ala Ile Ala Leu Ala Gln Gln Thr Gly Leu Pro Val Leu Ser Leu
             20                  25                  30

Asp Arg Val Gln Cys Cys Pro Gln Leu Ser Thr Gly Ser Gly Arg Pro
         35                  40                  45

Thr Val Glu Glu Leu Lys Gly Thr Thr Arg Leu Tyr Leu Asp Asp Arg
     50                  55                  60

Pro Leu Val Lys Gly Ile Ile Thr Ala Lys Gln Ala His Glu Arg Leu
 65                  70                  75                  80

Ile Ala Glu Val His Asn His Glu Ala
                 85

<210> SEQ ID NO 35
<211> LENGTH: 61
<212> TYPE: PRT
<213> ORGANISM: Pisum sativum

<400> SEQUENCE: 35

Met Ala Ser Met Ile Ser Ser Ser Ala Val Thr Thr Val Ser Arg Ala
 1               5                  10                  15

Ser Arg Gly Gln Ser Ala Ala Val Ala Pro Phe Gly Gly Leu Lys Ser
             20                  25                  30

Met Thr Gly Phe Pro Val Lys Lys Val Asn Thr Asp Ile Thr Ser Ile
         35                  40                  45

Thr Ser Asn Gly Gly Arg Val Lys Cys Met Val Leu Asp
     50                  55                  60
```